(12) United States Patent
Diaz et al.

(10) Patent No.: US 7,048,715 B2
(45) Date of Patent: May 23, 2006

(54) PUMP ASSEMBLY FOR AN INTEGRATED MEDICATION DELIVERY SYSTEM

(75) Inventors: Luis A. Diaz, Yabucoa, PR (US); David Hershberger, Kalamazoo, MI (US); Michael Strickler, Richland, MI (US); Jason Dee Toman, Portage, MI (US); Donald W. Malackowski, Schoolcraft, MI (US); Richard Franklin Huyser, Kalamazoo, MI (US)

(73) Assignee: Stryker Instruments, Kalamazoo, MI (US)

( * ) Notice: Subject to any disclaimer, the term of this patent is extended or adjusted under 35 U.S.C. 154(b) by 0 days.

(21) Appl. No.: 10/234,400

(22) Filed: Sep. 4, 2002

(65) Prior Publication Data

US 2002/0198493 A1    Dec. 26, 2002

Related U.S. Application Data

(62) Division of application No. 10/083,266, filed on Feb. 23, 2002, now Pat. No. 6,679,862.

(60) Provisional application No. 60/271,187, filed on Feb. 23, 2001.

(51) Int. Cl.
  *A61M 1/00*    (2006.01)
(52) U.S. Cl. ........................ 604/151; 604/131
(58) Field of Classification Search ............... 604/151, 604/67, 123, 253, 260, 250, 890.1, 891.2, 604/892.1, 152, 155, 156, 264, 131, 134–137
See application file for complete search history.

(56) References Cited

U.S. PATENT DOCUMENTS

| 2,423,701 | A | 7/1947 | Hardy |
| 2,734,526 | A | 2/1956 | Aagaard |
| 3,130,586 | A | 4/1964 | Taylor et al. |
| 3,149,492 | A | 9/1964 | Weinberg |
| 3,418,853 | A | 12/1968 | Curtis |
| 3,603,152 | A | 9/1971 | Alibert et al. |
| 3,731,679 | A | 5/1973 | Wilhelmson et al. |
| 4,027,536 | A | 6/1977 | Heggie |
| 4,139,008 | A | 2/1979 | Wagner |
| 4,141,252 | A | 2/1979 | Lodge |
| 4,174,637 | A | 11/1979 | Mulzet et al. |
| 4,177,810 | A | 12/1979 | Gourlandt |
| 4,179,939 | A | 12/1979 | Price |

(Continued)

FOREIGN PATENT DOCUMENTS

EP    0069350    1/1983

(Continued)

*Primary Examiner*—Kevin C. Sirmons
(74) *Attorney, Agent, or Firm*—Howard & Howard

(57) ABSTRACT

A medication delivery system delivers medication to a patient. The system includes a base and a reservoir disposed about the base for storing the medication. A pump for delivering the medication to the patient is supported by the base. The pump includes a housing having an inlet and an outlet. A first pinch lever is disposed near the inlet and a second pinch lever is disposed near the outlet. Each of the pinch levers move between an open and closed position to control a flow of the medication into the housing. A motor operatively engages the pinch levers to move the pinch levers such that the medication can be delivered to the patient. A biasing device engages at least one of the pinch levers and works in conjunction with the motor to normally bias the at least one pinch lever into the closed position during delivery of the medication to the patient and to maintain the at least one pinch lever in the closed position during a failure of the motor to prevent the inadvertent delivery of the medication to the patient.

23 Claims, 22 Drawing Sheets

U.S. PATENT DOCUMENTS

| | | |
|---|---|---|
| 4,202,333 A | 5/1980 | Thill et al. |
| 4,210,173 A | 7/1980 | Choksi |
| 4,236,880 A | 12/1980 | Archibald |
| 4,265,240 A | 5/1981 | Jenkins |
| 4,299,218 A | 11/1981 | Knigge et al. |
| 4,318,400 A | 3/1982 | Peery et al. |
| 4,381,006 A | 4/1983 | Genese |
| 4,384,578 A | 5/1983 | Winkler |
| 4,395,259 A | 7/1983 | Prestele et al. |
| 4,396,385 A | 8/1983 | Kelly et al. |
| 4,398,542 A | 8/1983 | Cunningham et al. |
| 4,398,908 A | 8/1983 | Siposs |
| 4,404,854 A | 9/1983 | Krempl et al. |
| 4,410,322 A | 10/1983 | Archibald |
| 4,411,651 A | 10/1983 | Schulman |
| 4,416,595 A | 11/1983 | Cromie |
| 4,425,800 A | 1/1984 | Claassen et al. |
| 4,446,344 A | 5/1984 | Fiedler |
| 4,456,223 A | 6/1984 | Ebling |
| 4,460,358 A | 7/1984 | Somerville et al. |
| 4,483,196 A | 11/1984 | Kurtz et al. |
| 4,484,479 A | 11/1984 | Eckhardt |
| 4,487,603 A | 12/1984 | Harris |
| 4,493,704 A | 1/1985 | Beard et al. |
| 4,535,641 A | 8/1985 | Kriz et al. |
| 4,548,607 A | 10/1985 | Harris |
| 4,550,748 A | 11/1985 | Nunez |
| 4,559,038 A | 12/1985 | Berg et al. |
| 4,559,040 A | 12/1985 | Horres et al. |
| 4,565,542 A | 1/1986 | Berg |
| 4,636,197 A | 1/1987 | Chu |
| 4,650,469 A | 3/1987 | Berg et al. |
| 4,657,486 A | 4/1987 | Stempfle et al. |
| 4,681,513 A | 7/1987 | Saito et al. |
| 4,741,733 A | 5/1988 | Winchell et al. |
| 4,813,937 A | 3/1989 | Vaillancourt |
| 4,938,223 A | 7/1990 | Charters et al. |
| 4,973,312 A | 11/1990 | Andrew |
| 5,017,059 A | 5/1991 | Davis |
| 5,053,031 A | 10/1991 | Borsanyi |
| 5,059,182 A | 10/1991 | Laing |
| 5,078,679 A | 1/1992 | Reese |
| 5,078,683 A | 1/1992 | Sancoff et al. |
| 5,085,631 A | 2/1992 | Leighton |
| 5,127,907 A | 7/1992 | Coutre et al. |
| 5,135,500 A | 8/1992 | Zdeb |
| 5,160,323 A | 11/1992 | Andrew |
| 5,163,901 A | 11/1992 | Eldor |
| 5,165,873 A | 11/1992 | Meijer |
| 5,165,874 A | 11/1992 | Sancoff et al. |
| 5,181,910 A | 1/1993 | Scanlon |
| 5,261,882 A | 11/1993 | Sealfon |
| 5,332,370 A | 7/1994 | Nakayama et al. |
| 5,342,313 A | 8/1994 | Campbell et al. |
| 5,364,242 A | 11/1994 | Olsen |
| 5,538,399 A | 7/1996 | Johnson |
| 5,556,263 A | 9/1996 | Jacobsen et al. |
| 5,575,770 A | 11/1996 | Melsky et al. |
| 5,603,354 A | 2/1997 | Jacobsen et al. |
| 5,618,163 A | 4/1997 | Jacobsen et al. |
| 5,632,606 A | 5/1997 | Jacobsen et al. |
| 5,647,575 A | 7/1997 | Jacobsen et al. |
| 5,655,779 A | 8/1997 | Jacobsen et al. |
| 5,695,473 A | 12/1997 | Olsen |
| 5,710,401 A | 1/1998 | Jacobsen et al. |
| 5,725,504 A | 3/1998 | Collins |
| 5,743,878 A | 4/1998 | Ross et al. |
| 5,755,691 A | 5/1998 | Hilborne |
| 5,772,635 A | 6/1998 | Dastur et al. |
| 5,788,673 A | 8/1998 | Young et al. |
| 5,799,690 A | 9/1998 | Jacobsen et al. |
| 5,800,397 A | 9/1998 | Wilson et al. |
| 5,807,075 A | 9/1998 | Jacobsen et al. |
| 5,853,373 A | 12/1998 | Griffith et al. |
| 5,931,647 A | 8/1999 | Jacobsen et al. |
| 5,941,533 A | 8/1999 | Jacobsen et al. |
| 5,944,495 A | 8/1999 | Jacobsen et al. |
| 6,007,310 A | 12/1999 | Jacobsen et al. |
| 6,090,071 A | 7/2000 | Kriesel |
| 6,585,499 B1 | 7/2003 | Nguyen et al. |

FOREIGN PATENT DOCUMENTS

| | | |
|---|---|---|
| GB | 0783971 | 10/1957 |

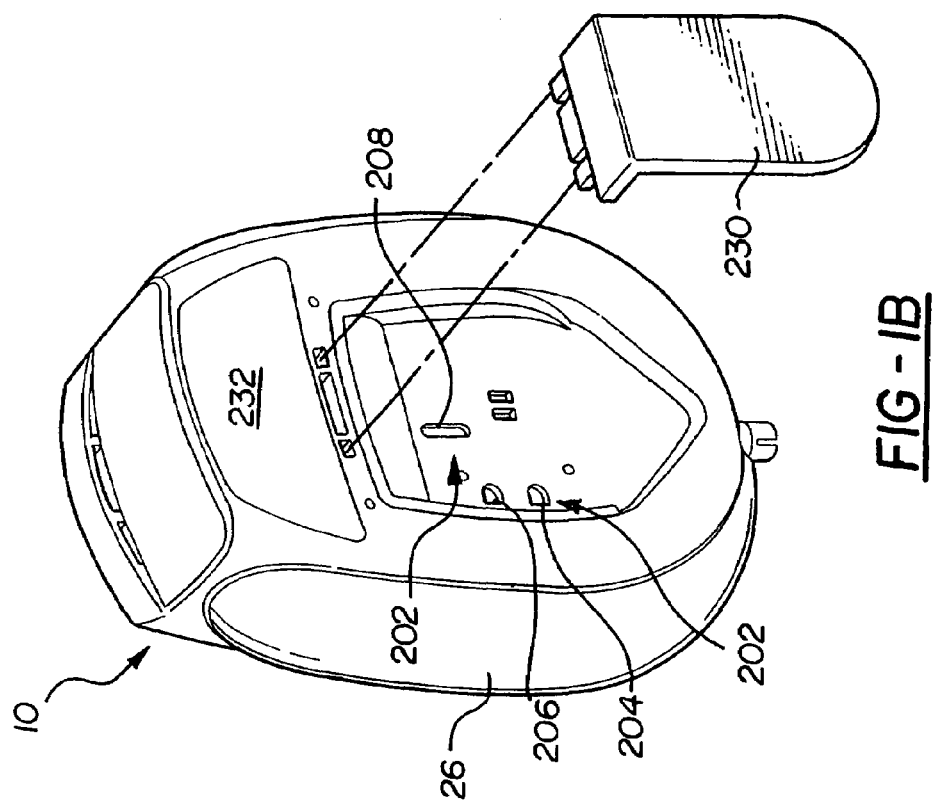
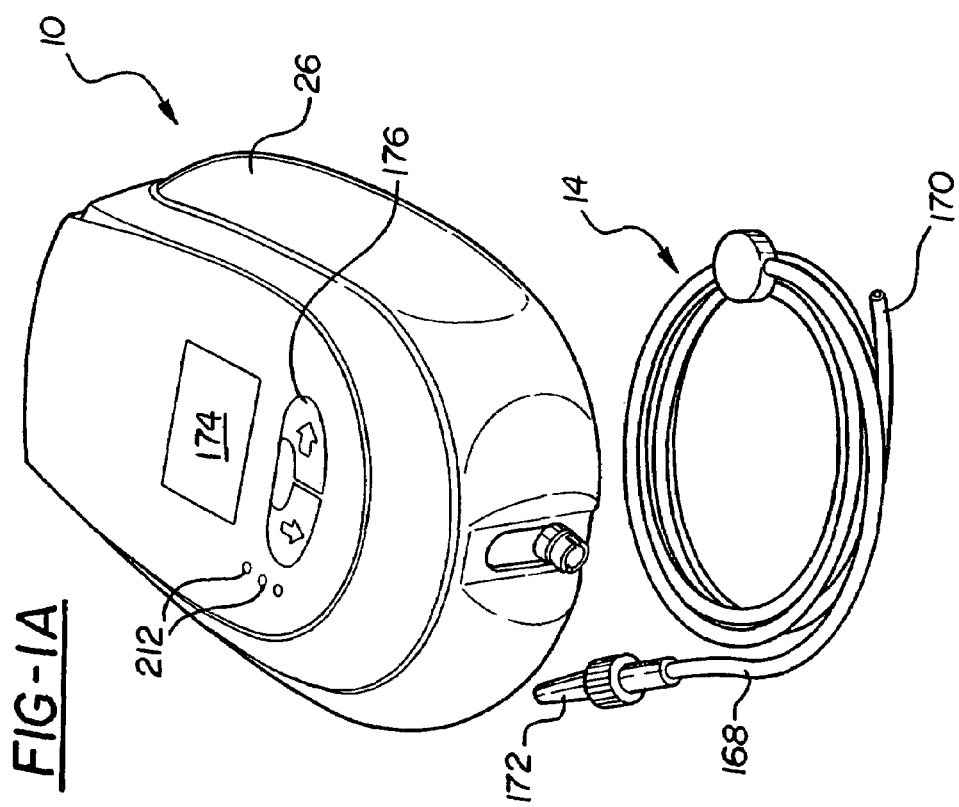

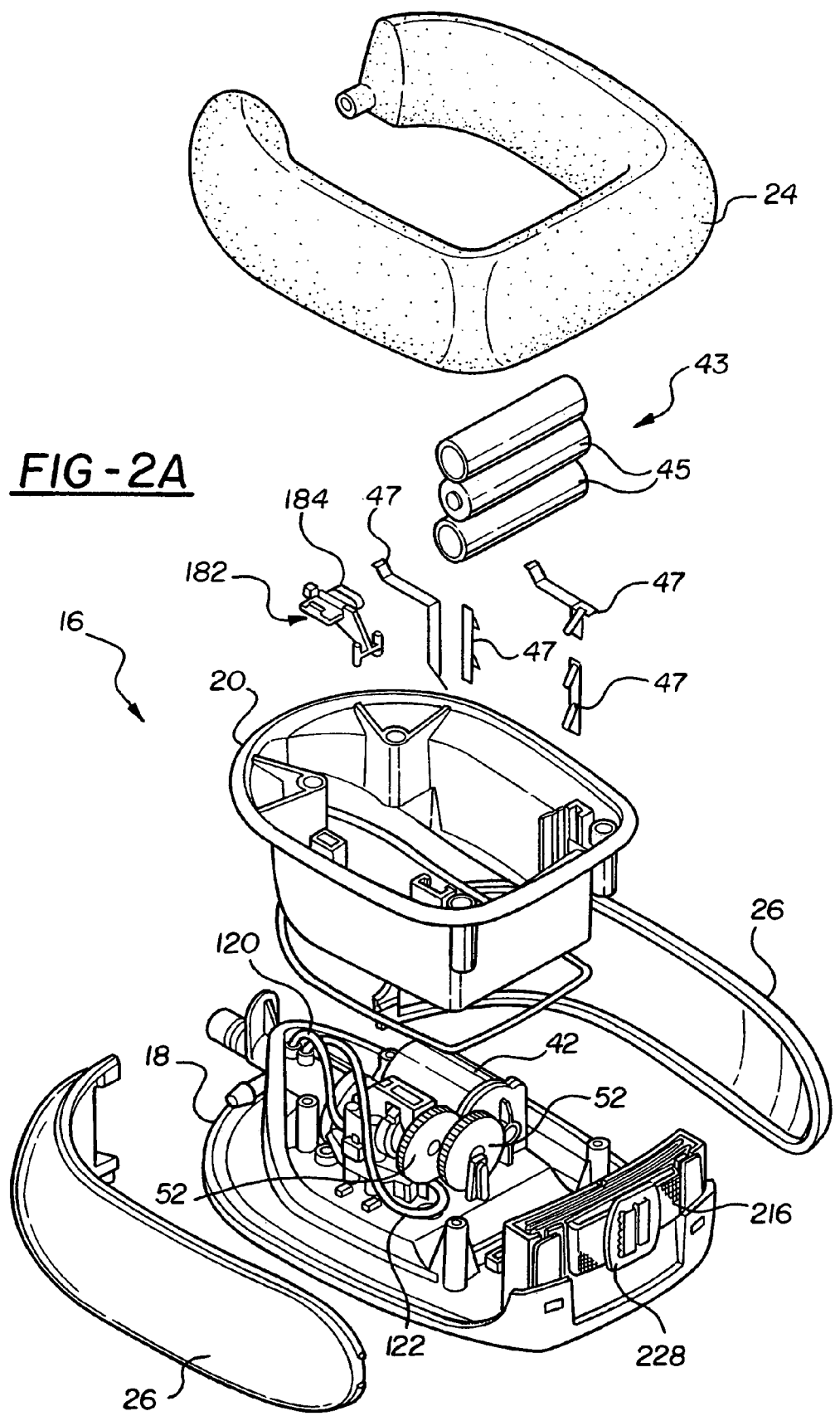

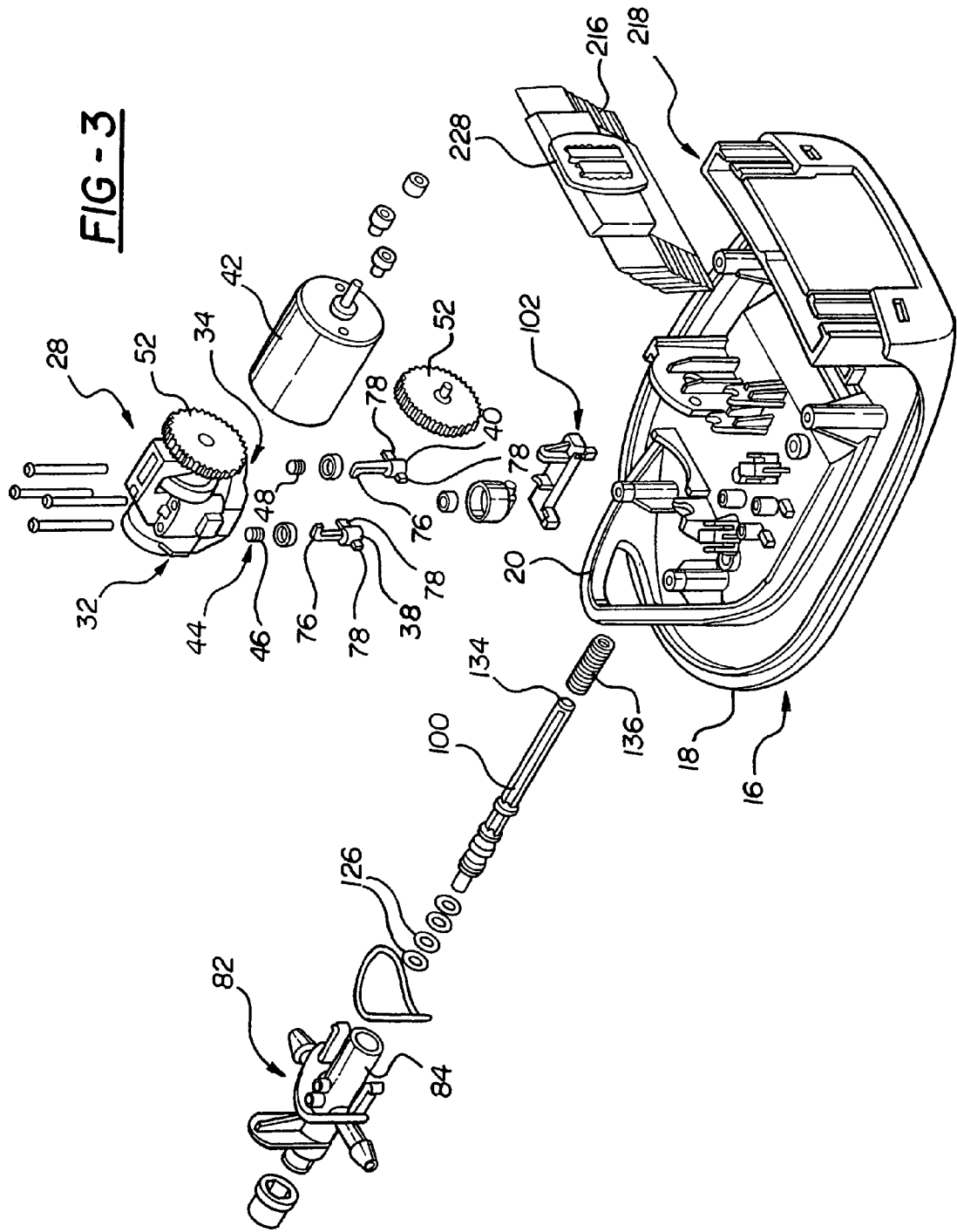

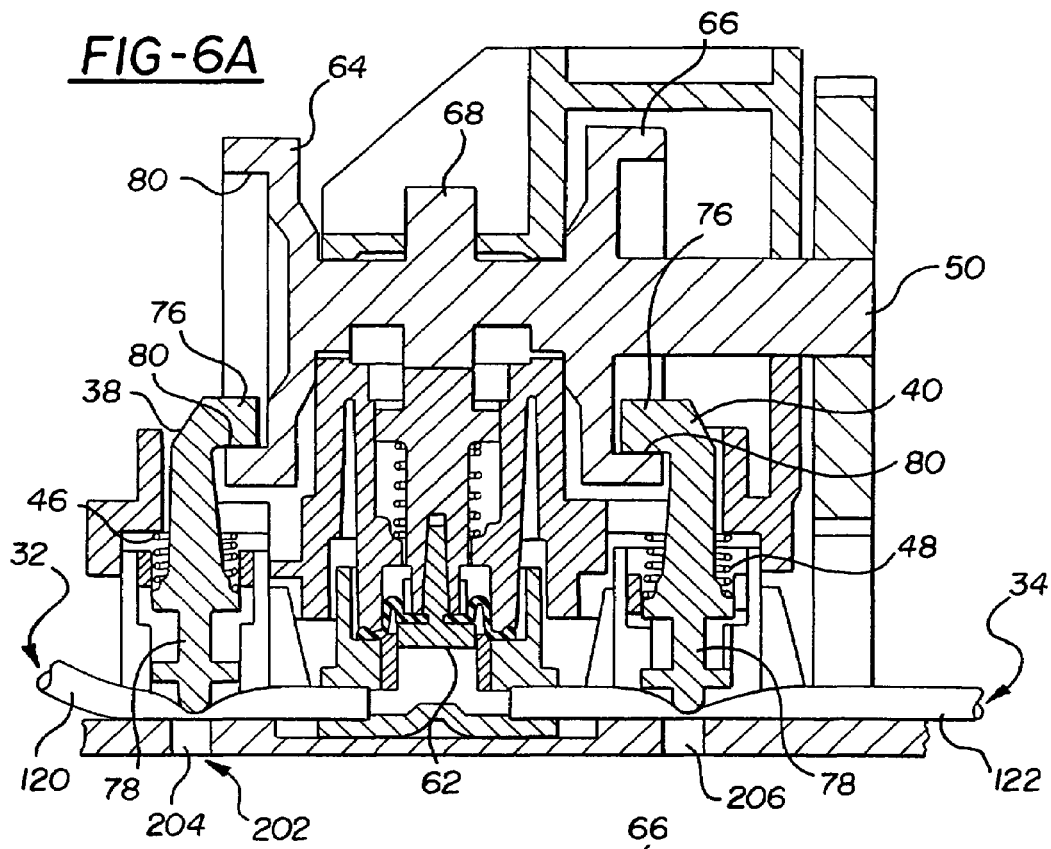
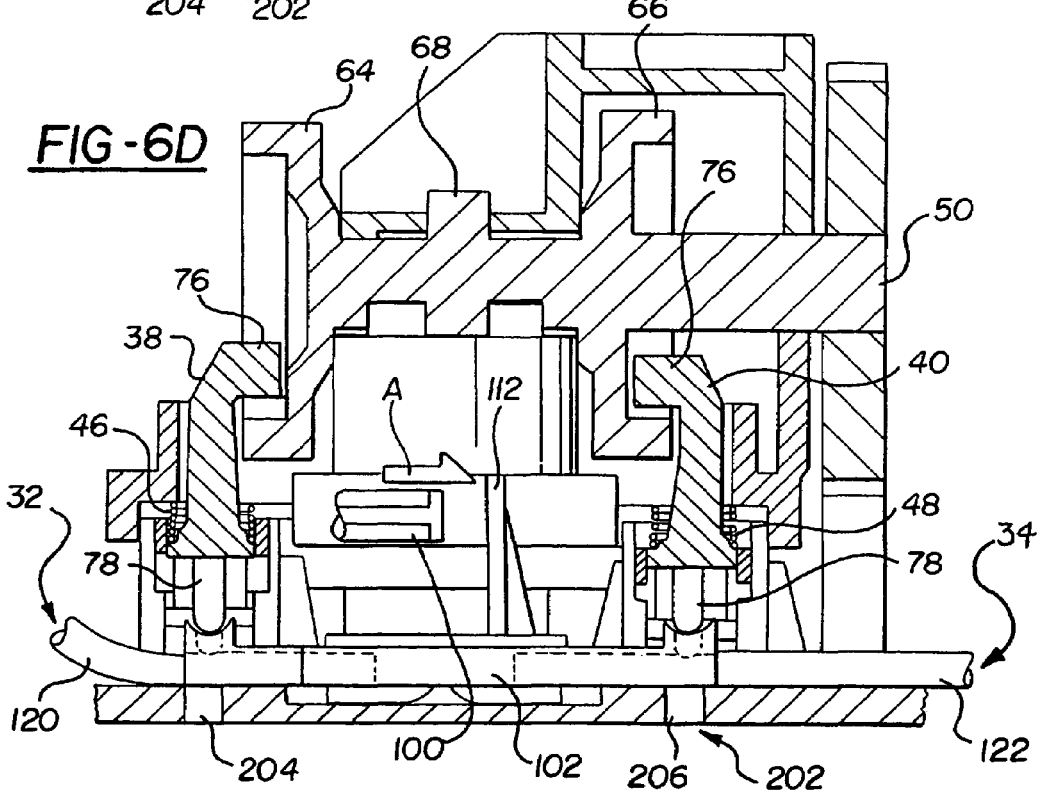

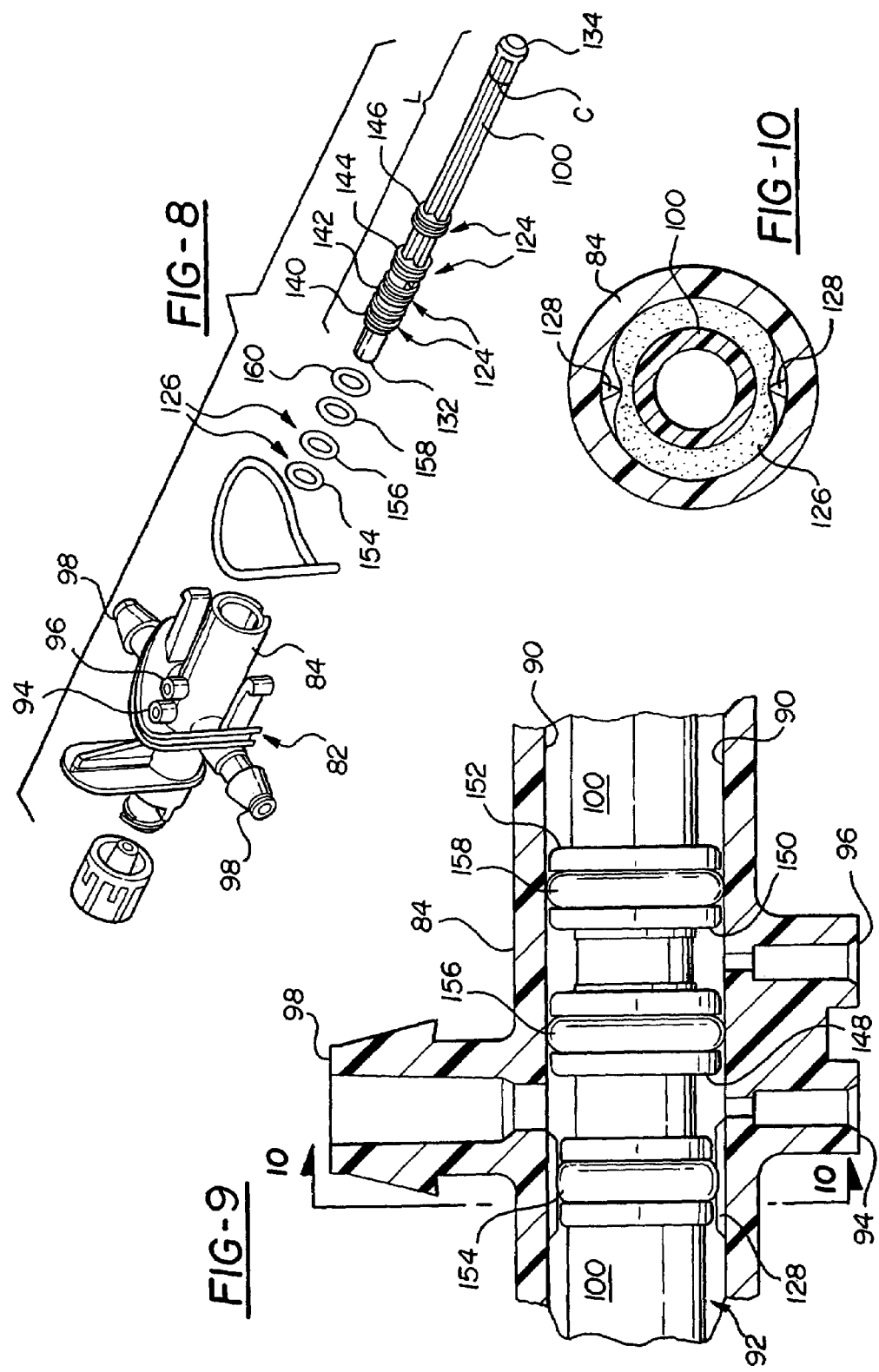

PUMP ASSEMBLY FOR AN INTEGRATED MEDICATION DELIVERY SYSTEM

RELATED APPLICATIONS

This application is a divisional of application Ser. No. 10/083,266 filed Feb. 23, 2002, now U.S. Pat. No. 6,679,862, which claims priority to and all advantages of United States Provisional Patent Application No. 60/271,187 which was filed on Feb. 23, 2001.

FIELD OF THE INVENTION

The subject invention generally relates to an integrated medication delivery system for delivering medication to a patient. The integrated medication delivery system is primarily used throughout the medical profession to deliver pain control medication and other medications intra-operatively, subcutaneously, and percutaneously to the patient after a surgical, or some other medical, procedure.

BACKGROUND OF THE INVENTION

Medication delivery systems are known in the art. As indicated above, medication delivery systems are used to deliver pain control medication and other medications intra-operatively, subcutaneously, and percutaneously to a patient after a surgical, or some other medical, procedure.

Conventional medication delivery systems are deficient for one reason or another. For example, U.S. Pat. No. 5,807,075 to Jacobsen et al. discloses a conventional medication delivery system that includes a base housing and a cassette. The base housing of the '075 patent houses electronic components, such as an electric motor, a power source, and an electronic controller, and the cassette of the '075 patent interacts with a supply of the medication to deliver the medication to the patient. This medication delivery system is deficient because the supply of the medication is not integrated into the cassette. That is, the cassette does not house the supply of the medication. Instead, the supply is external to the medication delivery system. This medication delivery system is also deficient because the base housing and the cassette are not properly integrated. As such, the complete medication delivery system, having the base housing and the cassette, cannot be simultaneously sterilized prior to use of the system. Instead, the base housing and the cassette require separate sterilization. Furthermore, because the base housing and the cassette are not integrated, the cassette must be mounted to the base housing which requires additional assembly by a surgeon or some other medical assistant. This additional assembly is time consuming and is often inconvenient for the surgeons and medical assistants.

A further example of a conventional medication delivery system is disclosed in U.S. Pat. No. 4,650,469 to Berg et al. This patent discloses a medication delivery system that includes a control module and a reservoir module removably connected to the control module. The control module includes a pump mechanism, valves, a power source, electronic controls, and the like, and the reservoir module includes a container that supplies the medication to be delivered to the patient. Although the medication delivery system disclosed in the '469 patent connects the control module and the reservoir module, this medication delivery system is deficient in that, once connected, the control module and the reservoir module cannot be simultaneously sterilized. The modules cannot be simultaneously sterilized because, as described at column 11, lines 22–28, one of the valves in the control module closes the fluid connection (the tube 22) between the control module and the reservoir module at all times. That is, the '469 patent does not include a device, such as an actuator, to prevent the valves from closing on this fluid connection. As such, a sterilization fluid, such as ethylene oxide (EtO) gas cannot flow into both the control module and the reservoir module once these modules are connected.

The conventional medication delivery system disclosed in the '469 patent is also deficient because it relies exclusively on a motor and a cam shaft to move the valves from the open position to the closed position when delivering the medication to the patient. This medication delivery system does not incorporate an additional biasing device to ensure that the valves are biased into the closed position if the motor, gear, cam shaft, or power supply fails. Without such an additional biasing device, this system's ability to prevent the inadvertent delivery of the medication to the patient in the event of one of the above failures is compromised. Instead, this medication delivery system relies only on the motor and the cam shaft to allow or to prevent delivery of the medication, and reliance on these two components is insufficient.

Other conventional medication delivery systems are also deficient for a multitude of other reasons. For instance, these conventional systems do not incorporate port assemblies that adequately control the flow of medication throughout the system. In these conventional systems, a single port assembly does not enable various medical fluids to flow into, from, and within the system. Conventional medication delivery systems also do not provide detection systems that adequately determine when a medication delivery system is realizing a blockage in the flow of medication to the patient or that adequately determine when a supply in the medication delivery system has been depleted. The detection systems in the prior art medication delivery systems do not make optimum use of the position of the tubes that carry the medication relative to the position of the electronic controller. Conventional medication delivery systems also do not provide a testing access port that allows manufacturers to confirm operation of the medication delivery system after assembly, and prior to use, of the system. As such, the operation of many prior art medication delivery systems cannot be confirmed prior to shipment to medical professionals for use. Conventional medication delivery systems are also not ideal for carrying. Some prior art systems do not even include a carrying strap. As such, the patient cannot be easily treated outside of a hospital or other medical facility, the patient is prevented from being ambulatory. Other medication delivery systems in the prior art that do include some form of carrying strap do not make carrying convenient because, in these systems, the carrying strap is not conveniently stored in a storage cavity of the system. That is, the carrying strap is not integrated into the system itself for easy access by the patient. The medication delivery systems of the prior art are also not easily controlled. That is, there is not method associated with these systems that effectively controls an amount of the medication to be delivered to the patient. The prior art methods for controlling the amount of medication that is to be delivered to the patient are deficient because these methods require constant attention, require complicated setup and monitoring by the surgeon or other medical professional, and may even risk the health and safety of the patient. Other conventional medication delivery systems do not have electronic controllers, specifically specialized circuitry incorporated into the controller, that adequately prevent too much medication from being delivered to the patient in the event of failure of certain mechanical components. Also, the electronic controllers and circuitry of other conventional medication delivery systems are not suitably designed to maximize the conservation of power and to prevent the entire medication delivery system from being reset by removing and replacing the power source, e.g. a battery.

Due to the deficiencies in conventional medication delivery systems, including those described above, it is desirable to provide a novel medication delivery system that is appropriately integrated for simultaneous sterilization. It is also desirable to provide a novel medication delivery system that overcomes the other deficiencies identified above in the prior art.

SUMMARY OF THE INVENTION AND ADVANTAGES

An integrated medication delivery system is disclosed. The medication delivery system delivers medication to a patient. The medication delivery system is primarily used to deliver pain control medication and other medications intraoperatively, subcutaneously, and percutaneously to the patient after a surgical, or some other medical, procedure. The medication delivery system according to the subject invention is suitable for complete sterilization by a sterilization fluid.

To accomplish complete sterilization, the medication delivery system includes a base housing and a medication reservoir. The medication reservoir is disposed about the base housing for storing the medication that is to be delivered to the patient. As such the medication reservoir, i.e., the supply of the medication, is integrated with the base housing.

The medication delivery system includes a pump assembly for delivering the medication to the patient. More specifically, the pump assembly, which is supported by the base housing, includes a pump housing having a pump inlet and a pump outlet. The pump inlet and the pump outlet alternate between an open and a closed state to deliver the medication the patient. A port extends from the base housing and is in fluid communication with the medication reservoir and the pump assembly during sterilization. As such, the port provides access for the sterilization fluid to flow into the medication reservoir and the pump assembly.

The medication delivery system further includes an actuator disposed in the base housing. The actuator operatively engages the pump inlet and the pump outlet to retain both the pump inlet and the pump outlet in the open state during sterilization. As a result, the sterilization fluid can penetrate into the medication reservoir, the pump inlet, the pump housing, and the pump outlet to completely sterilize the medication delivery system. That is, because of the actuator, the complete medication delivery system of the subject invention, including the base housing, the pump assembly, and the medication reservoir can be simultaneously sterilized prior to use of the system. Also, because the medication reservoir is disposed about and properly integrated with the base housing, the supply of the medication is not external to the rest of the medication delivery system, and the medication delivery system does not require additional assembly by a surgeon and the like prior to use.

The pump assembly for the medication delivery system also serves to prevent the inadvertent delivery of the medication to the patient. In addition to the pump housing, the pump inlet, and the pump outlet, the pump assembly may further include, depending on the particular embodiment, first and second pinch levers and at least one biasing device.

The first pinch lever is disposed at the pump inlet and is moveable between an open position and a closed position to control a flow of the medication into the pump housing through the pump inlet. The second pinch lever is disposed at the pump outlet and is moveable between an open position and a closed position to control a flow of the medication from the pump housing through the pump outlet. A motor, which operatively engages the first and second pinch levers, is included to move the first and second pinch levers into the open position such that the medication can delivered to the patient.

The biasing device engages at least one of the first and second pinch levers and works in conjunction with the motor to normally bias at least one of the first and second pinch levers into the closed position during delivery of the medication to the patient. This maintains at least one of the first and second pinch levers in the closed position during a failure of the motor thereby preventing the inadvertent delivery of the medication to the patient. As a result, the medication delivery system of the subject invention does not exclusively rely on the motor to move the valves from the open position to the closed position when delivering the medication to the patient. That is, the biasing device ensures that the first and second pinch levers are biased into the closed position even if the motor, or other mechanical components, such as a gear, cam shaft, or power supply, fails. With the biasing device, the subject invention guarantees prevention of the inadvertent delivery of the medication to the patient in the event of one of the above failures.

A port assembly for the medication delivery system may also be included to enable various fluids, such as the sterilization fluid and the medication, to flow into, from, and within the medication delivery system. The port assembly includes an elongated housing and a plunger disposed within the housing. The plunger is moveable within the housing between an off-position, a fill-position, and a fluid delivery-position. The flow of the fluids into, from, and within the medication delivery system is controlled and modified depending on the position of the plunger. As such, the port assembly provides adequate control of the flow of medication throughout the medication delivery system.

The subject invention further provides a blockage detection system for the medication delivery system. Utilizing an electronic controller, a detection film, and a medication outlet tube, and relying on expansion of the medication outlet tube in response to increased pressure in the medication outlet tube, the empty detection system detects a blockage in the flow of the medication to the patient. The empty detection system adequately determines when the medication delivery system is realizing a blockage. To accomplish this, the empty detection system makes optimum use of the position of the medication outlet tube relative to the position of the electronic controller. The detection film may be replaced with a coating applied to the medication outlet tube that activates the electronic controller.

The subject invention further provides an empty detection system for the medication delivery system. Utilizing the electronic controller, the detection film, and a medication inlet tube, and relying on the collapsibility or contraction of the medication inlet tube in response to variations in pressure in the medication inlet tube that result from a lack of flow of the medication, the empty detection system detects when the supply of the medication has been depleted. To accomplish this, the empty detection system makes optimum use of the position of the medication inlet tube relative to the position of the electronic controller. As in the empty detection system, the detection film in the empty detection system may also be replaced with a coating applied to the medication inlet tube that serves to activate and deactivate the electronic controller.

After assembly of the medication delivery system, the subject invention can be tested using a testing instrument. To accomplish testing of the medication delivery system, at least one testing access port is defined within the base housing. The testing access port is aligned with at least one of the pump inlet, the pump outlet, and the actuator to provide access for the testing instrument. The testing instrument effectively disengages the actuator from the pump inlet and the pump outlet such that they can alternate between open and closed states and the operation of the medication delivery system can be testing with an operable pump assembly. The testing access port, incorporated into the base housing, allows the manufacturer to confirm operation after assembly, and prior to use, of the medication delivery system.

The medication delivery system of the subject invention is also ideal for carrying by the patient. A carrying strap is mounted within the base housing for the carrying of the medication delivery system by the patient. More specifically, carrying strap is at least partially disposed in an integral storage cavity that is defined within the base housing. The carrying strap at least partially extends from the integral storage cavity to interact with the patient for carrying the medication delivery system. The carrying strap and integral storage cavity of the subject invention enable the patient to continue easy treatment outside of a hospital or other medical facility. As a result, the patient can remain ambulatory. Disposing the carrying strap in the integral storage cavity makes carrying the medication delivery system of the subject invention a convenient experience for the patient as the carrying strap is always easily accessible.

The subject invention further includes a method of controlling the medication delivery system. The method includes the step of selecting the amount of the medication that is to be delivered to the patient in accordance with a first set of explanatory indicia on a removable overlay label. Next, the system is locked such that the selected amount of the medication to be delivered to the patient is unable to be modified. After the system is locked, the removable overlay label is removed to reveal a patient label. Then, the medication delivery system is operated in accordance with a second set of explanatory indicia on the patient label. This method effectively controls the amount of the medication that is to be delivered to the patient and also provides for easy control and programming of the medication delivery system. As a result of this method of controlling the medication delivery system, the patient does not need to constantly pay attention to and maintain the medication delivery system. Also, set-up of the medication delivery system is not complicated and monitoring of the medication delivery system is not required such that the health and safety of the patient is not compromised.

The subject invention also includes the electronic controller and specialized circuitry incorporated into the electronic controller for various reasons. For instance, some circuitry is targeted to prevent too much medication from being delivered to the patient if certain mechanical components fail. Other electronic design features of the electronic controller of the subject invention are targeted to conserve power throughout the medication delivery system and to prevent the entire medication delivery system from being reset upon the removal or replacement of the power source.

Accordingly, the subject invention provides an integrated medication delivery system that overcomes the deficiencies in the prior art, including those described above.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1A is a perspective view of an integrated medication delivery system according to the subject invention with an infusion tube set;

FIG. 1B is a perspective view of an underside of the system illustrating a system mounting clip for securing the system to a patient;

FIG. 2A is an exploded perspective view of the system illustrating a medication reservoir, a base housing, reservoir casings, a pump assembly, and a carrying strap of the system;

FIG. 3 is an exploded perspective view of the system illustrating a port, a plunger, the pump assembly including a motor and first and second pinch levers, an actuator, and the base housing including an integral storage cavity for the carrying strap;

FIG. 6A is a partially cross-sectional side view of a cam shaft, the pump assembly, and the first and second pinch levers illustrating the pinch levers in a closed position to pinch medication inlet and outlet tubes;

FIG. 6D is a partially cross-sectional side view of the system, as disclosed in FIG. 6A, in combination with the plunger and the actuator, with the actuator retaining the pinch levers in the open position;

FIG. 8 is an exploded perspective view of the port and the plunger;

FIG. 9 is an enlarged partially cross-sectional top view of the plunger disposed in the port illustrating a first, second, and third fluid connector;

FIG. 10 is a partially cross-sectional side view taken along line 10—10 in FIG. 9 illustrating a seal disposed about the plunger being depressed by leak ribs extending from the port;

DETAILED DESCRIPTION OF THE PREFERRED EMBODIMENT

Figure 19:
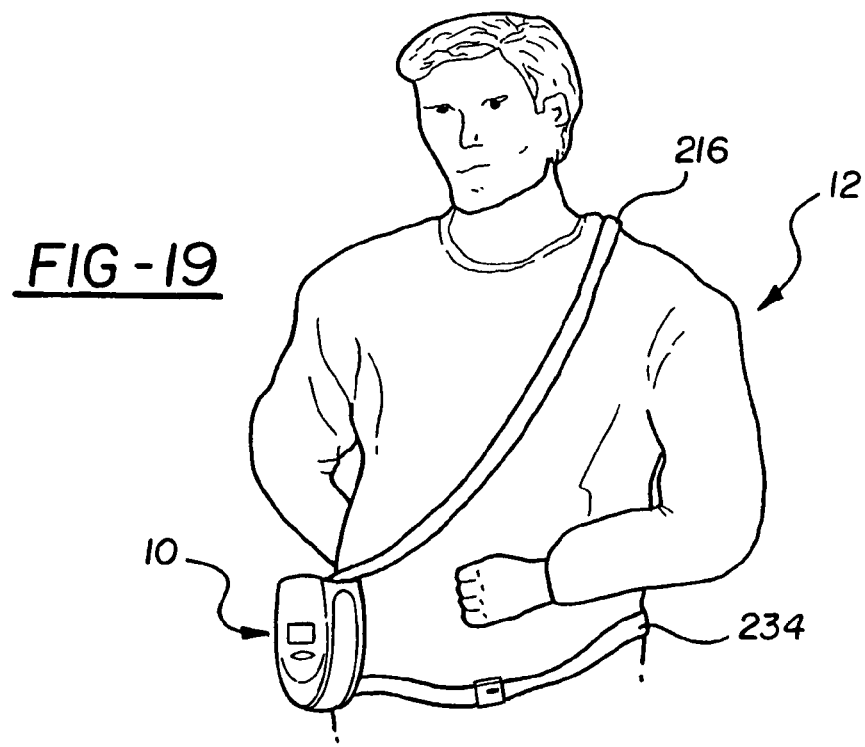
FIG. 19 is a perspective view of the patient using the carrying strap as a shoulder strap to carry the system.
Figure 18A:
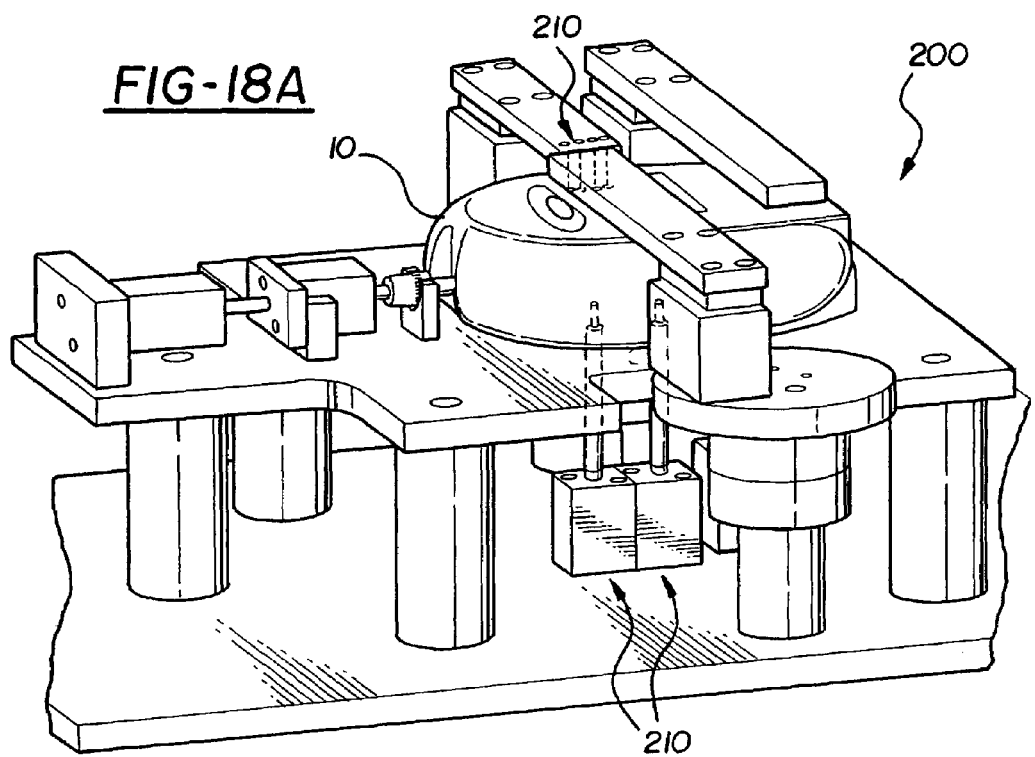
FIG. 18A is a top perspective view of the system engaged with a testing instrument for confirming proper operation of the system after assembly and prior to use.
Figure 18B:
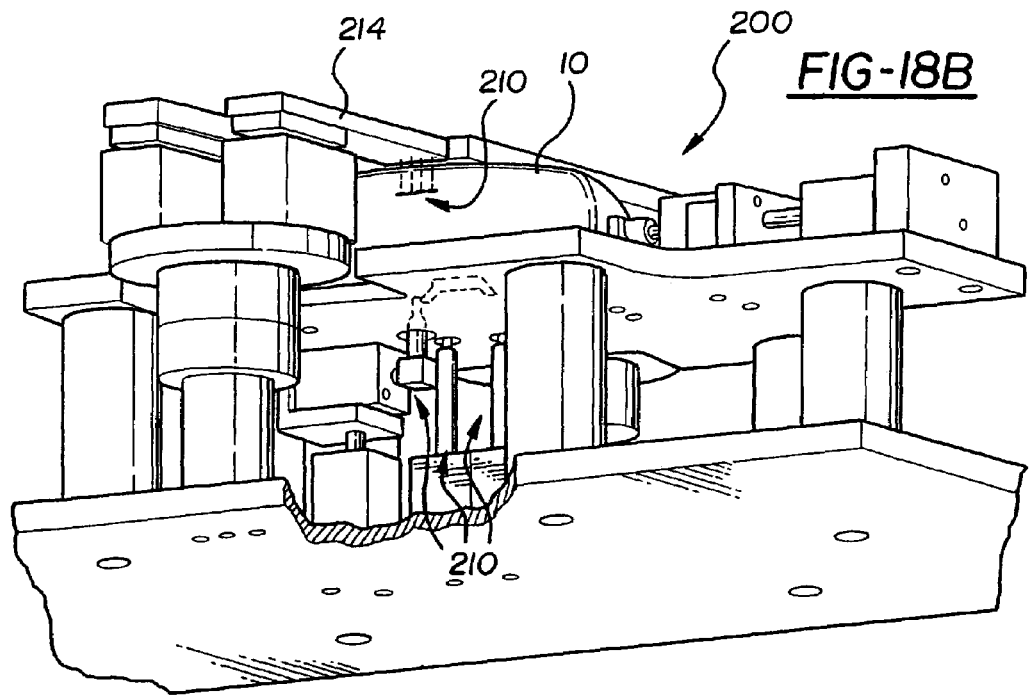
FIG. 18B is a bottom perspective view of the system engaged with a second testing instrument for confirming proper operation of the system after assembly and prior to use.

Referring to the Figures, wherein like numerals indicate like or corresponding parts throughout the several views, an integrated medication delivery system 10 is generally disclosed at 10. The integrated medication delivery system 10, hereinafter described as the system 10, delivers medication to a patient 12 (refer to FIG. 19). More specifically, the system 10 is primarily used throughout the medical profession to deliver pain control medication and other medications to the patient 12 after a surgical, or some other medical, procedure. As disclosed in FIG. 1A, the system 10 is used in combination with an infusion tube set 14 to deliver the medication to the patient 12. The infusion tube set 14 is described below.

The system 10 of the subject invention is also suitable for complete sterilization by a sterilization fluid including, but not limited to, ethylene oxide (EtO) gas. Although not ideal, certain liquids may even be used to sterilize the system 10. For descriptive purposes only, the terminology of "medication" and of "sterilization" fluid may also be described throughout simply as a fluid.

Figure 2B:
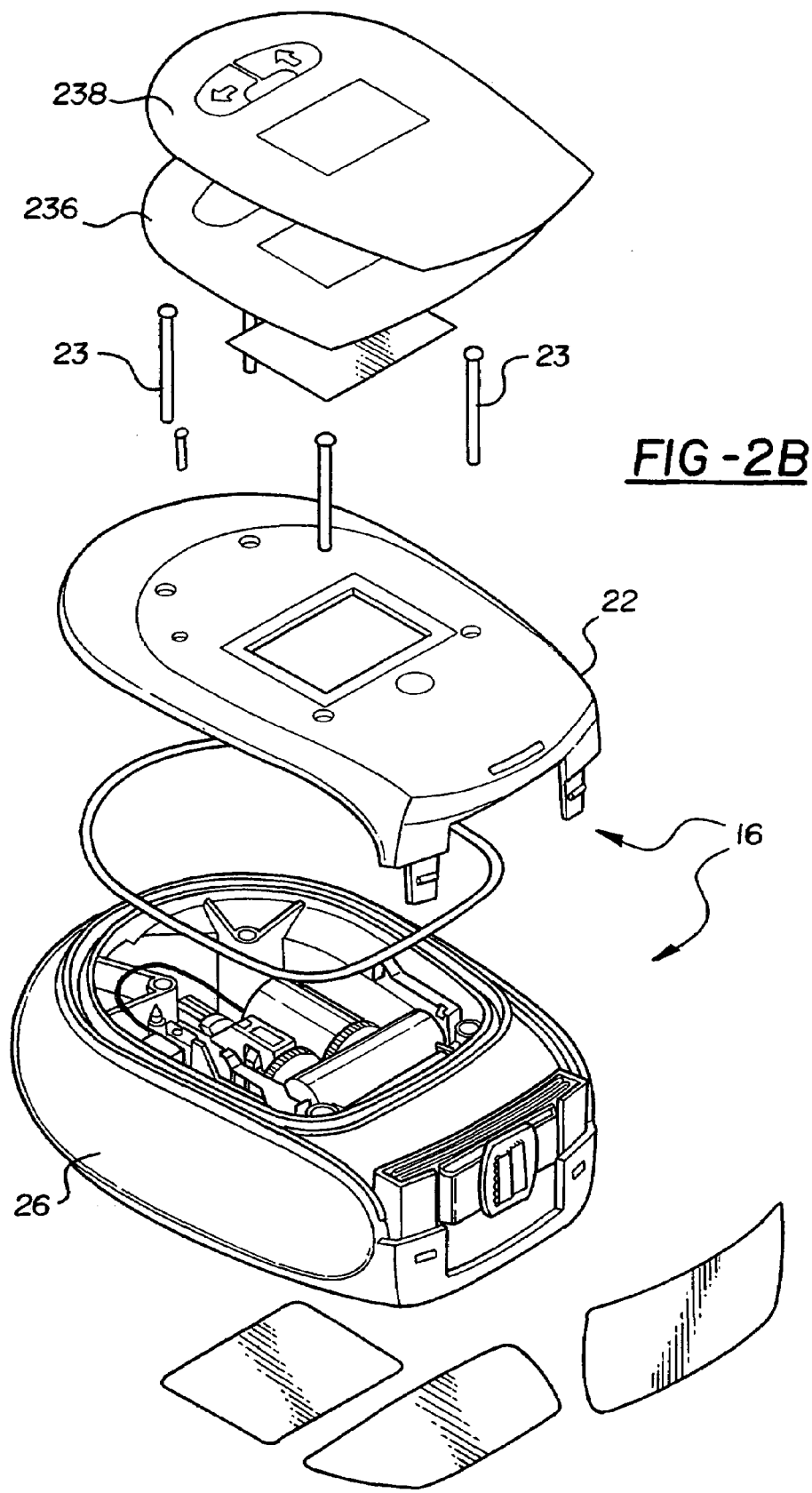
FIG. 2B is an exploded perspective view of the system illustrating a removable overlay label, a patient label, and a top housing of the base housing for assembly to the system.

Referring primarily to FIGS. 2A–3, the system 10 includes a base housing 16. The base housing 16 is further defined as a bottom housing 18, a middle housing 20 mounted to the bottom housing 18 and a top housing 22, i.e., a cover. The housings 18, 20, 22 are preferably mounted together via screws 23. The system 10 also includes a medication reservoir 24 disposed about the base housing 16. More specifically, the reservoir 24 is disposed about the middle housing 20. The reservoir 24 stores the supply of medication that is to be delivered to the patient 12. Preferably, the reservoir 24 is formed of a flexible, yet durable plastic material. The system 10 further includes a reservoir casing 26 disposed between the bottom and top housings 18, 22. The reservoir casing 26 at least partially surrounds the reservoir 24 to protect the medication that is to be delivered to the patient 12. The preferred embodiment of the subject invention includes two reservoir casings 26 that surround the reservoir 24 to protect the medication. Of course, it is to be understood that the reservoir casing 26 may be a unitary component and still adequately surround the reservoir 24 to protect the medication. The reservoir casing 26 is particularly useful when the patient 12 is carrying the system 10. Carrying of the system 10 is described below.

Referring primarily to FIGS. 2A, 3, and 5–6D, a pump assembly 28 is supported by the base housing 16. Specifically, the pump assembly 28 is mounted to the bottom housing 18. As understood by those skilled in the art, the pump assembly 28 is responsible for delivering the medication to the patient 12. As described below, the pump assembly 28 also serves to prevent inadvertent delivery of the medication to the patient 12.

Figure 5:
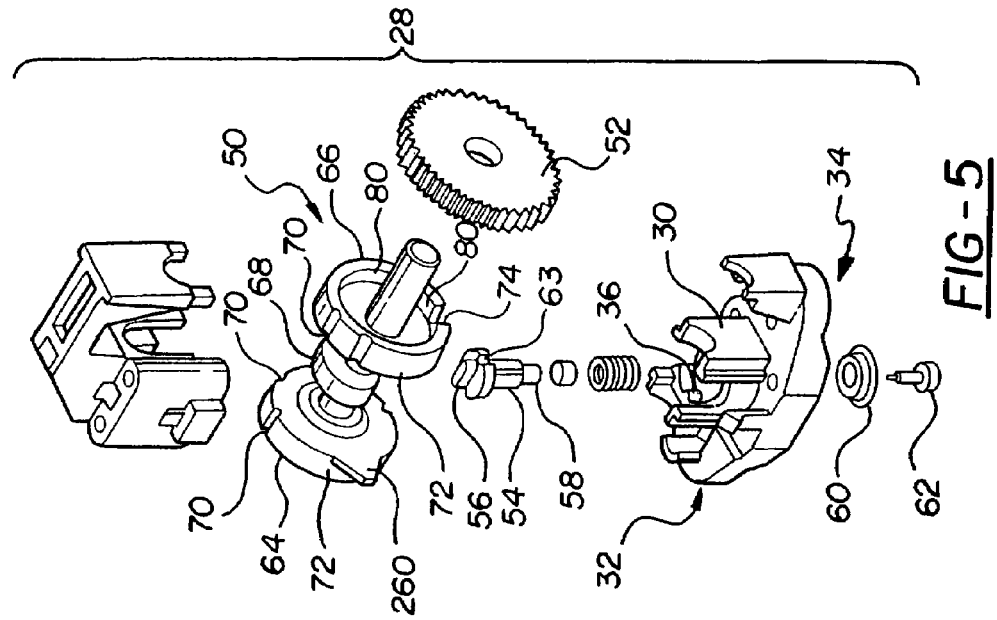
FIG. 5 is an exploded perspective view of the pump assembly.

As disclosed best in FIG. 5, the pump assembly 28 includes a pump housing 30 having a pump inlet 32 and a pump outlet 34. The pump housing 30 also has at least one detent 36. The at least one detent 36 is described below. The pump inlet 32 and the pump outlet 34 alternate between an open and a closed state to deliver the medication to the patient 12. Referring now to FIGS. 3, and 6A–6D, a first pinch lever 38, also referred to as a pinch valve, is disposed at the pump inlet 32 and a second pinch lever 40 or valve is disposed at the pump outlet 34. The first pinch lever 38 functions to alternate the pump inlet 32 between the open and the closed state, and the second pinch lever 40 functions to alternate the pump outlet 34 between the open and the closed state.

Figure 6B:
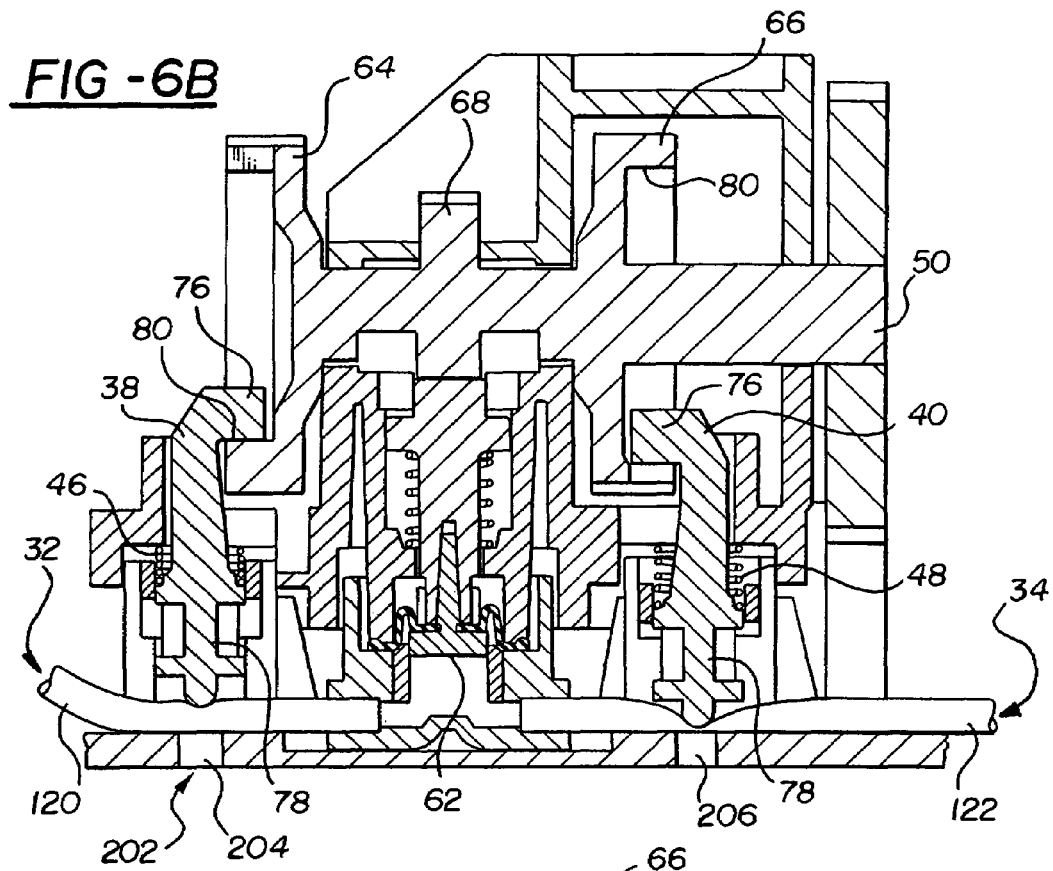
FIG. 6B is a partially cross-sectional side view of the system, as disclosed in FIG. 6A, illustrating the first pinch lever in an open position and the second pinch lever in a closed position to draw medication into the pump assembly.
Figure 6C:
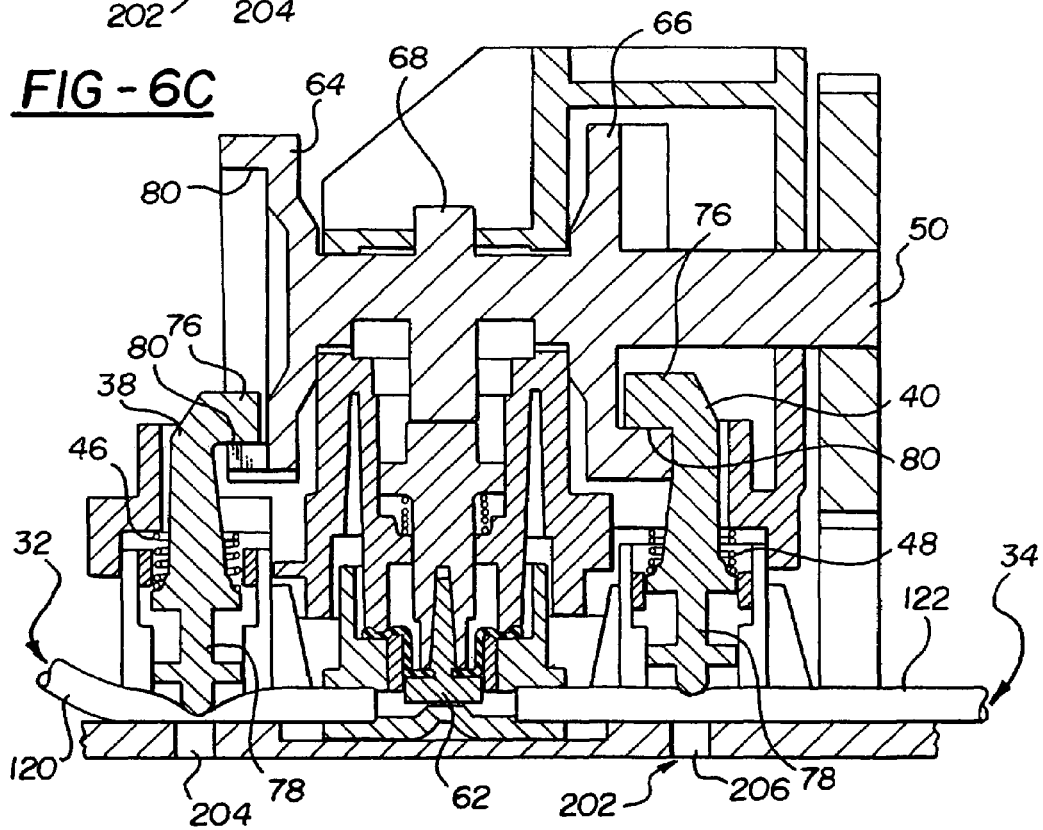
FIG. 6C is a partially cross-sectional side view of the system, as disclosed in FIG. 6A, illustrating the first pinch lever in a closed position and the second pinch lever in an open position to displace medication from the pump assembly.

As FIGS. 6B and 6C disclose, the first pinch lever 38 is moveable between an open position (FIG. 6B) and a closed position (FIG. 6C) to control a flow of the medication into the pump housing 30 through the pump inlet 32, and the second pinch lever 40 is moveable between an open position (FIG. 6C) and a closed position (FIG. 6B) to control a flow of the medication from the pump housing 30 through the pump outlet 34. The pump assembly 28 further includes a motor 42 that is operatively engaged to the first and second pinch levers 38, 40 for moving these levers 38, 40 into the open position such that the medication can be delivered to the patient 12. The motor 42 includes a driving output shaft, not shown in the Figures, for driving the pump assembly 28. A power source 43 is integrated into the system 10 to provide power to the system 10, including the motor 42. Preferably, the power source includes batteries 45 and battery contacts 47.

As shown in FIG. 6A, the first pinch lever 38 is normally-biased to maintain the pump inlet 32 in the closed state and the second pinch lever 40 is normally-biased to maintain the pump outlet 34 in the closed state. To accomplish this, at least one biasing device 44 is included in the pump assembly 28. Preferably, the at least one biasing device 44 is a compression spring as shown, but not numbered, throughout the Figures. However, it is to be understood that the at least one biasing device 44 may be any device that is suitable for normally-biasing at least one, if not both, of the first and second pinch levers 38, 40 into the closed position. The at least one biasing 44 device engages at least one of the first and second pinch levers 38, 40 and works in conjunction with the motor 42 to normally bias at least one of the first and second pinch levers 38, 40 into the closed position. As such, if the motor 42 fails during delivery of the medication, then the first and second pinch levers 38, 40 are biased into and thereafter maintained in the closed position to prevent the inadvertent delivery of the medication to the patient 12. The motor 42 is able to move the first and second pinch levers 38, 40 into the open position despite the bias of the at least one biasing device 44.

In the preferred embodiment of the subject invention, the at least one biasing device 44 comprises a first 46 and a second 48 biasing device. The first biasing device 46, preferably a compression spring, engages the first pinch lever 38, and the second biasing device 48, also preferably a compression spring, engages the second pinch lever 40. As disclosed in FIG. 6A, the first and second biasing devices 46, 48 maintain the first and second pinch levers 38, 40 in the closed position during failure of the motor 42 thereby preventing the inadvertent delivery of the medication to the patient 12. More specifically, the closed first pinch lever 38 prevents the medication from being drawn into the pump assembly 28 through the pump inlet 32, and the closed second pinch lever 40 prevents the medication from being displaced from the pump assembly 28 through the pump outlet 34.

Referring primarily to FIGS. 5-6D, to effectively operate the system 10 and move the first and second pinch levers 38, 40 for delivery of the medication to the patient 12, the pump assembly 28 of the subject invention further includes a cam shaft 50 supported on the pump housing 30. The cam shaft 50 is geared to the motor 42, via a number of gears 52, to operatively engage the motor 42 to the first and second pinch levers 38, 40. The cam shaft 50 is described in greater detail below.

Figure 7:
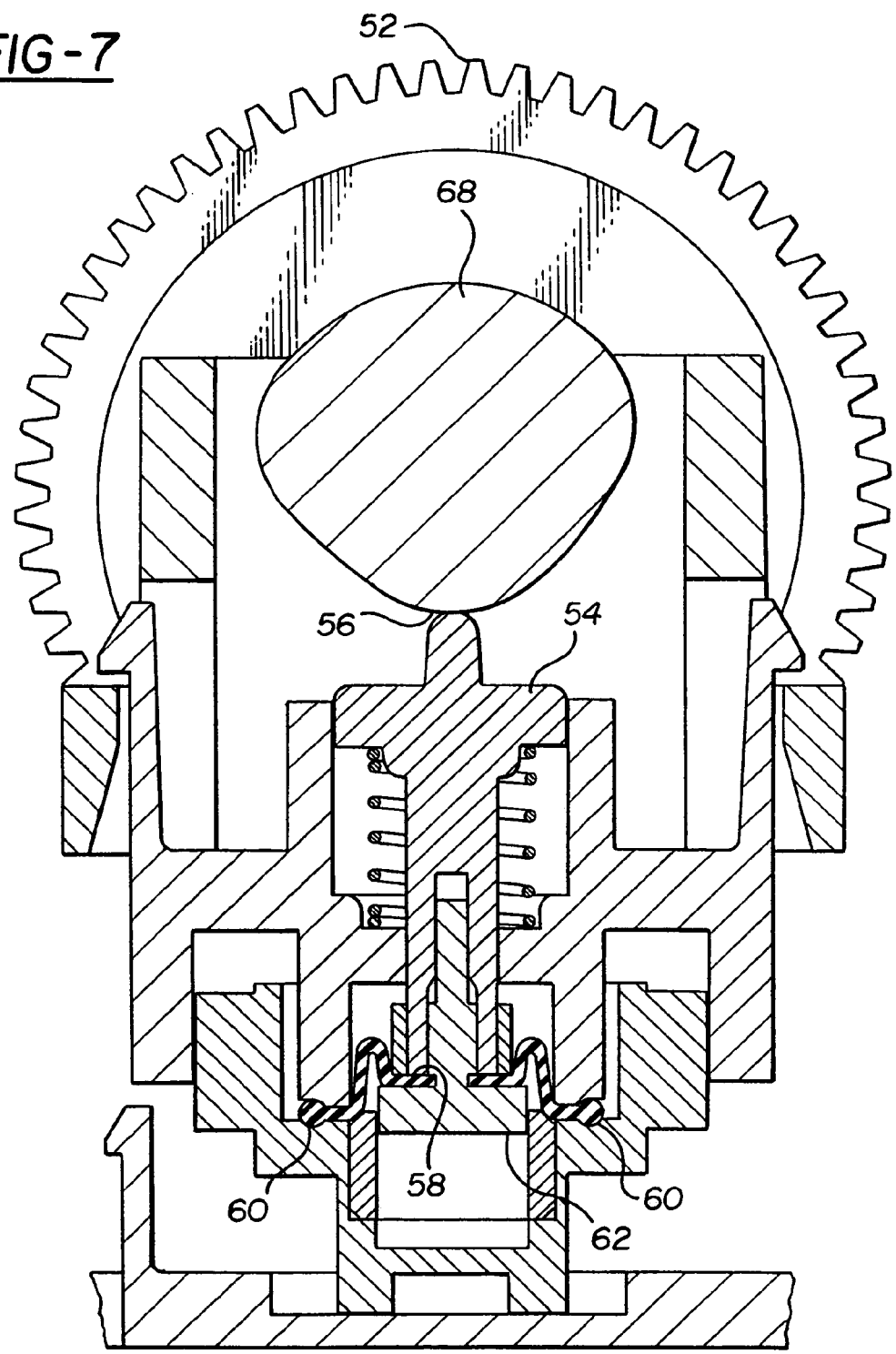
FIG. 7 is a partially cross-sectional side view of the pump assembly.

As disclosed best in FIGS. 5 and 7, the pump assembly 28 also includes a piston 54 disposed in the pump housing 30. The motor 42 moves the piston 54 within the pump housing 30 to draw the medication into the pump housing 30 when the first pinch lever 38 is in the open position and the second pinch lever 40 is in the closed position (see FIG. 6B). The motor 42 also moves the piston 54 within the pump housing 30 to displace the medication from the pump housing 30 when the first pinch lever 38 is in the closed position and the second pinch lever 40 is in the open position (see FIG. 6C). The piston 54 includes an actuation end 56 and a pumping end 58. A diaphragm seal 60 is disposed at the pumping end 58 of the piston 54. The diaphragm seal 60 is secured at the pumping end 58 of the piston 54 by a piston cap 62. The piston 54 also includes at least one slot 63 at the actuation end 56. The at least one detent 36 of the pump housing 30, originally introduced above, engages the at least one slot 63 at the actuation end 56 of the piston 54 to prevent unwanted rotation of the piston 54 as the piston 54 is moved within the pump housing 30 by the motor 42 and the cam shaft 50.

The cam shaft 50 supports first and second outside cams 64, 66 and an inside cam 68. The inside cam 68 of the cam shaft 50 is disposed between the first and second outside cams 64, 66. The first outside cam 64 engages the first pinch lever 38 to move the first pinch lever 38 between the open and closed position, and the second outside cam 66 engages the second pinch lever 40 to move the second pinch lever 40 between the open and closed positions. The inside cam 68 engages the actuation end 56 of the piston 54 to move the piston 54 within the pump housing 30.

Referring to FIG. 5, the first and second outside cams 64, 66 include a plurality of slits 70 along an outer circumference 72 of the cams 64, 66. These slits 70 are used during assembly and testing of the system 10 to confirm dimensional tuning of the cams 64, 66. Also, at least one of the first and second outside cams 64, 66, preferably the first outside cam 64, includes an assembly slot 74 defined within the outer circumference 72 of the cams 64, 66. This assembly slot 74 facilitates assembly of the pump assembly 28. In particular, this assembly slot 74 facilitates mounting of the cam shaft 50, including the cams 64, 66, after the first and second pinch levers 38, 40 have already been incorporated into the system 10.

Each of the first and second pinch levers 38, 40 comprise a cam follower 76 and lever guides 78. The lever guides 78 are described below. The cam followers 76 of the pinch levers 38, 40 are engaged by the cam shaft 50 for alternating movement of the first and second pinch levers 38, 40 between the open and closed positions such that the medication can be delivered to the patient 12. More specifically, the cam follower 76 of the first pinch lever 38 is engaged by the first outside cam 64 for alternating movement of the first pinch lever 38 between the open and closed positions, and the cam follower 76 of the second pinch lever 40 is engaged by the second outside cam 66 for alternating movement of the second pinch lever 40 between the open and closed positions. Even more specifically, each of the first and second outside cams 64, 66 include internal cam surfaces 80. As disclosed in FIGS. 6A–6D, the cam follower 76 of the first pinch lever 38 rides within the internal cam surface 80 of the first outside cam 64 for alternating movement of the first pinch lever 38, and the cam follower 76 of the second pinch lever 40 rides within the internal cam surface 80 of the second outside cam 66 for alternating movement of the second pinch lever 40.

Referring primarily to FIGS. 3, and 8–10, the system 10 further includes a port assembly 82 that enables various fluids, such as the medication or the sterilization fluid, to flow into, from, and within the system 10. The port assembly 82, hereinafter described as the port 82, extends from the base housing 16. More specifically, the port 82 extends from the middle housing 20. The port 82 is in fluid communication with the reservoir 24 and the pump assembly 28. During sterilization, the port 82 provides access for the sterilization fluid to flow into the reservoir 24 and the pump assembly 28. During filling, the port 82 provides access for the medication to flow into the reservoir 24 and the pump assembly 28. During delivery of the medication to the patient 12, the port 82 provides access for the medication to be delivered to the patient 12.

Referring particularly to FIGS. 9, and 11A–13B, the port 82 includes an elongated housing 84. The elongated housing 84 includes a proximate end 86, a distal end 88, and an interior wall 90 defining a fluid chamber 92 between the proximate and distal ends 86, 88. It is the proximate end 86 of the elongated housing 84 that extends from the system 10 to provide access for the fluid to flow both into and from the system 10. The port 82 further includes a first fluid connector 94, a second fluid connector 96, and a third fluid connector 98. The first fluid connector 94, alternatively referred to as an outlet of the port 82, extends from the elongated housing 84 to allow the fluid to flow from the fluid chamber 92 into the pump assembly 28. The second fluid connector 96, alternatively referred to as an inlet to the port 82, extends from the elongated housing 84 to allow the fluid to flow from the pump assembly 28 into the fluid chamber 92. The third fluid connector 98, alternatively referred to as an access to the reservoir 24, extends from the elongated housing 84 to allow the fluid to flow between the fluid chamber 92 and the reservoir 24. In the preferred embodiment of the subject invention, there are two third fluid connectors 98, one third fluid connector 98 extending from opposite sides of the elongated housing 84.

Figure 11A:
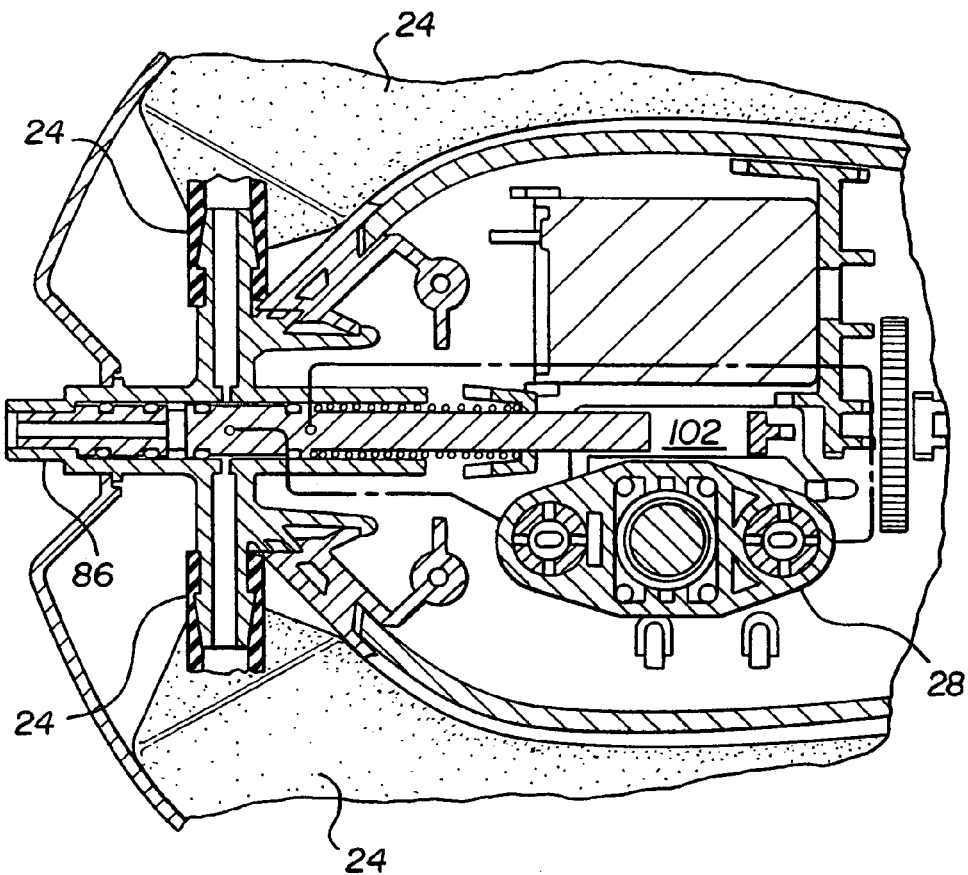
FIG. 11A is a partially cross-sectional top view of the system with the plunger in an off-position.
Figure 11B:
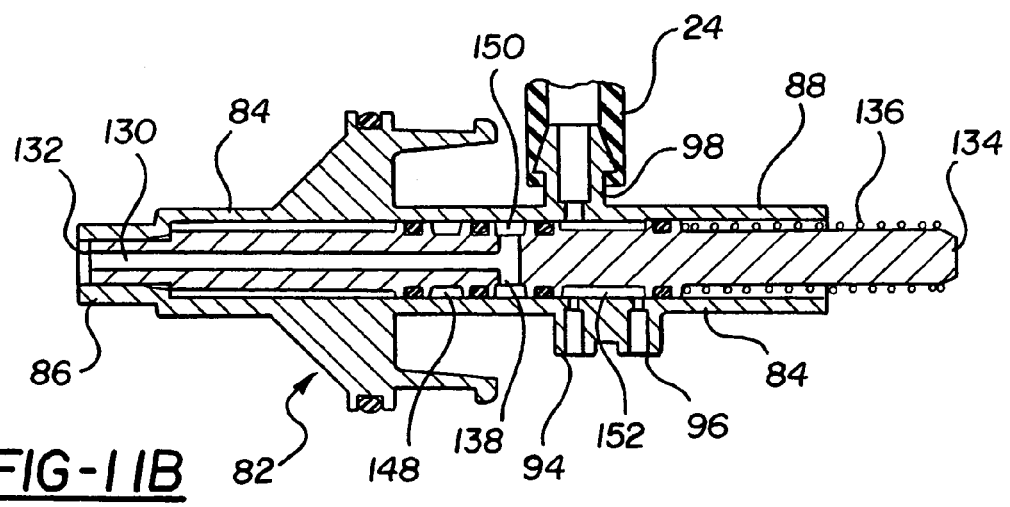
FIG. 11B is a partially cross-sectional view of the port and the plunger disposed in the port in the off-position from FIG. 11A.
Figure 12A:
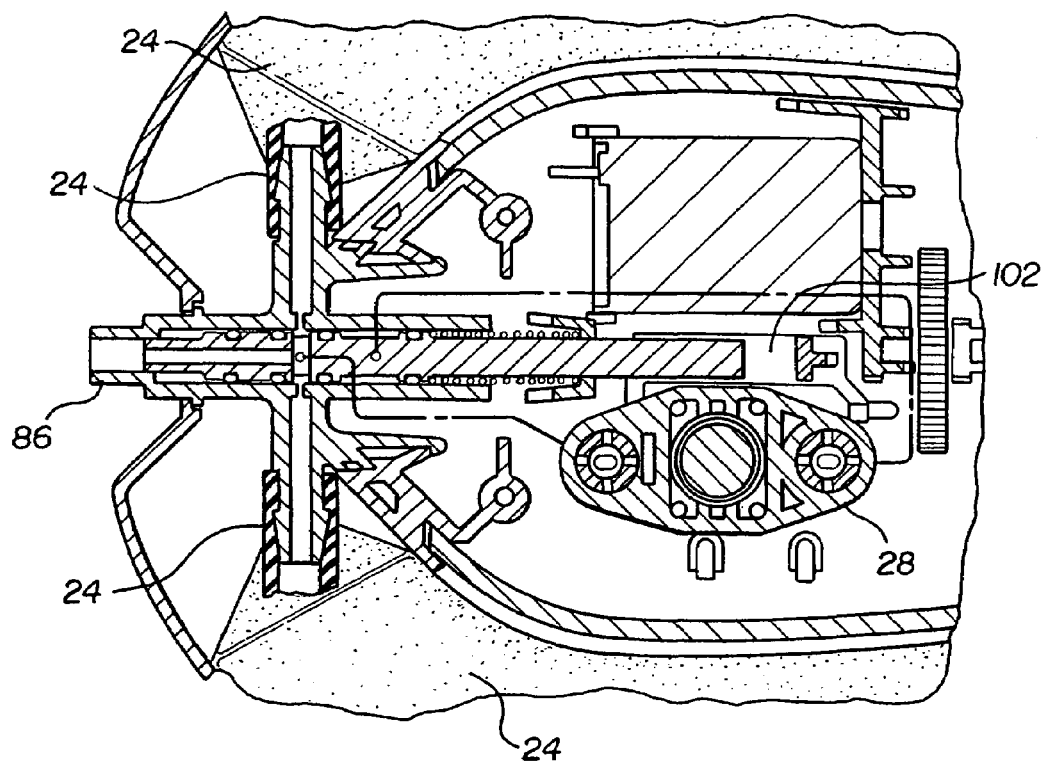
FIG. 12A is a partially cross-sectional top view of the system with the plunger in a fill-position such that the system can be sterilized and filled with medication.
Figure 12B:
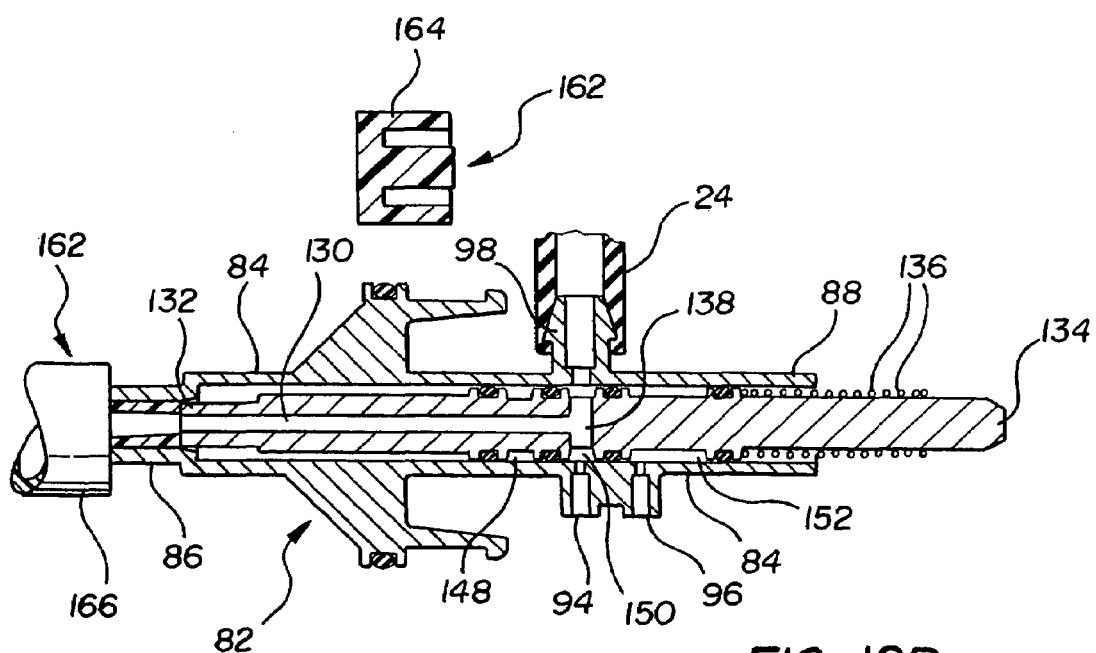
FIG. 12B is a partially cross-sectional view of the port and the plunger disposed in the port in the fill-position from FIG. 12A additionally illustrating a syringe for moving the plunger into the fill-position and a fluid cap for sterilization.
Figure 13A:
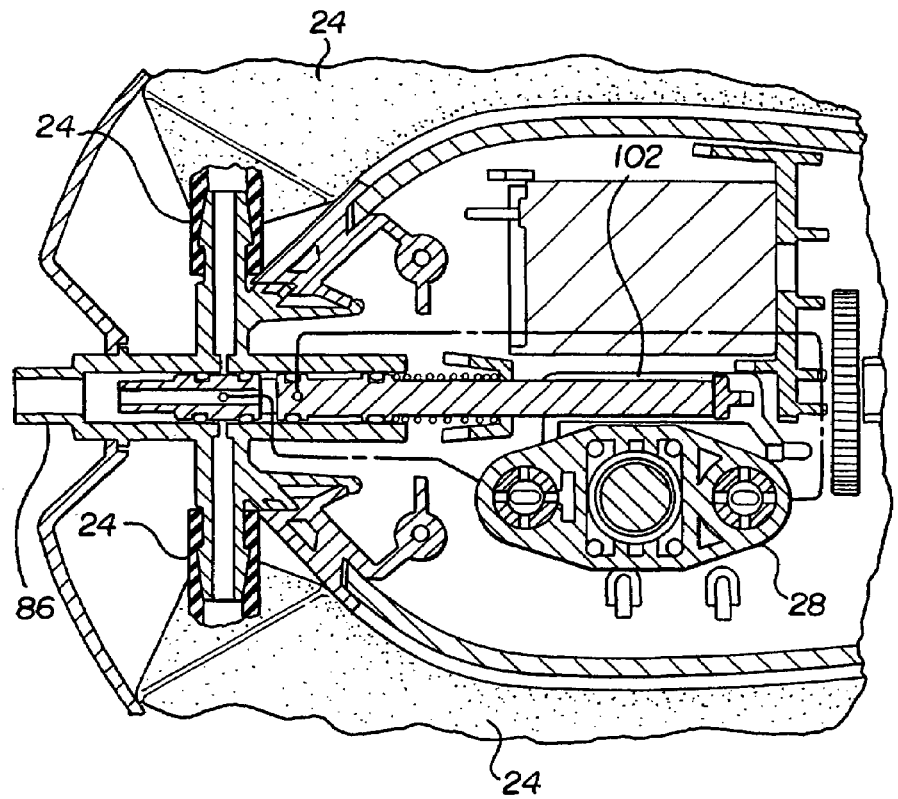
FIG. 13A is a partially cross-sectional top view of the system with the plunger in a fluid delivery-position such that the medication can be delivered to the patient.
Figure 13B:
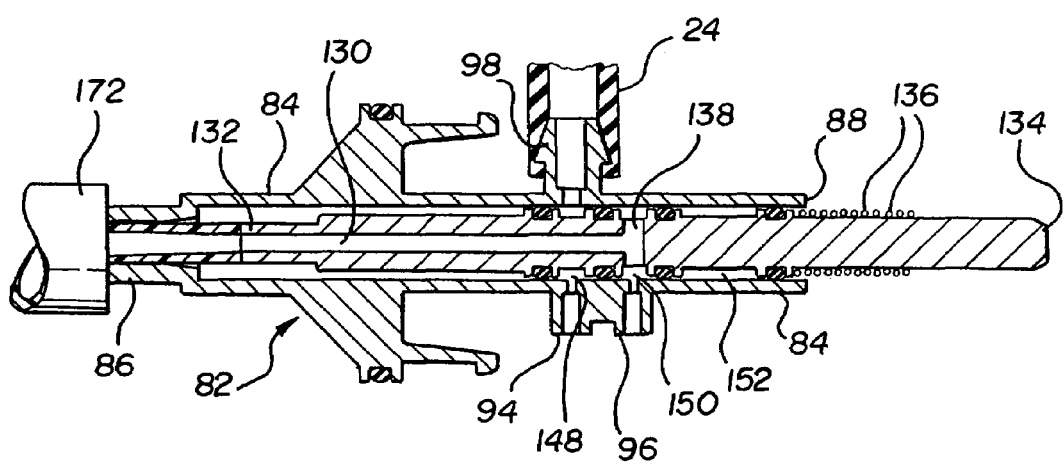
FIG. 13B is a partially cross-sectional view of the port and the plunger disposed in the port in the fluid delivery-position from FIG. 13A additionally illustrating a connector from the infusion tubing set.

Referring primarily to FIGS. 3, 6D, 8–10, and 11A–13B, the port 82 further includes a plunger 100. The plunger 100 is disposed in the fluid chamber 92 of the port 82 and is moveable between an off-position (FIGS. 11A–11B), a fill-position (FIGS. 12A–12B), and a fluid delivery-position (FIGS. 13A–13B). As disclosed in FIGS. 11A–11B, in the off-position, the first, second, and third fluid connectors 94, 96, 98 are isolated from the proximate end 86 of the elongated housing 84 by the plunger 100. As a result, the flow of fluid through the port 82 is prevented. As disclosed in FIGS. 12A–12B, in the fill-position, the first and third fluid connectors 94, 98 are in fluid communication with the proximate end 86 of the elongated housing 84. As a result, a fluid flow path, shown but not numbered in FIGS. 12A–12B, is provided between the proximate end 86 of the elongated housing 84, the medication reservoir 24, and the pump assembly 28 such that the fluid can be filled through the proximate end 86 of the housing and into the medication reservoir 24 and the pump assembly 28. This fluid flow path is defined between the port 82, the reservoir 24, and the pump assembly 28 such that the flow of sterilization fluid through the fluid flow path is continuous during sterilization of the system 10. The fill-position of the plunger 100 is utilized when the system 10 is being sterilized with the sterilization fluid and also when the system 10 is being filled with medication. As disclosed in FIGS. 13A–13B, in the fluid delivery position, the first, second, and third fluid connectors 94, 96, 98 are in fluid communication with the proximate end 86 of the elongated housing 84 and with each other for supplying the pump assembly 28 and for delivering the fluid to the patient 12.

Referring primarily to FIGS. 3, 6D, 11A, 12A, 13A, and 14A–14B, the system 10 further includes an actuator 102 disposed in the base housing 16. The actuator 102 is moveable between a disengaged position and an engaged position. The disengaged position of the actuator 102 is described below. As disclosed in FIG. 6D, in the engaged position, the actuator 102 operatively engages the pump inlet 32 and the pump outlet 34 to retain, i.e., lock, both the pump inlet 32 and the pump outlet 34 in the open state during sterilization. With the pump inlet 32 and the pump outlet 34 in the open state, the sterilization fluid can penetrate throughout the entire system 10 to completely sterilize the system 10. That is, the sterilization fluid can penetrate into the reservoir 24, the pump inlet 32, the pump housing 30, and the pump outlet 34 to completely sterilize the system 10.

More specifically, the actuator 102 interacts with the first and second pinch levers 38, 40 to retain both the pump inlet 32 and the pump outlet 34 in the open state during sterilization. In the engaged position, the actuator 102 moves the first pinch lever 38 away from the pump inlet 32 into the open position to retain the pump inlet 32 in the open state, and the actuator 102 moves the second pinch lever 40 away from the pump outlet 34 into the open position to retain the pump outlet 34 in the open state. The actuator 102 retains both the first and second pinch levers 38, 40 in the open position for sterilization despite the bias of the at least one biasing device 44.

On the other hand, when the actuator 102 is in the disengaged position, as indicated by the absence of the actuator 102 from FIGS. 6B–6C, the actuator 102 is operatively disengaged from the pump inlet 32 and the pump outlet 34. The actuator 102 is in the disengaged position when it is necessary to deliver the medication to the patient 12 such that the pump inlet 32 and the pump outlet 34 can alternate between the open and closed states to deliver the medication the patient 12. Disengagement of the actuator 102 permits the pump inlet 32 and the pump outlet 34 to alternate between the open and closed states.

Figure 14A:
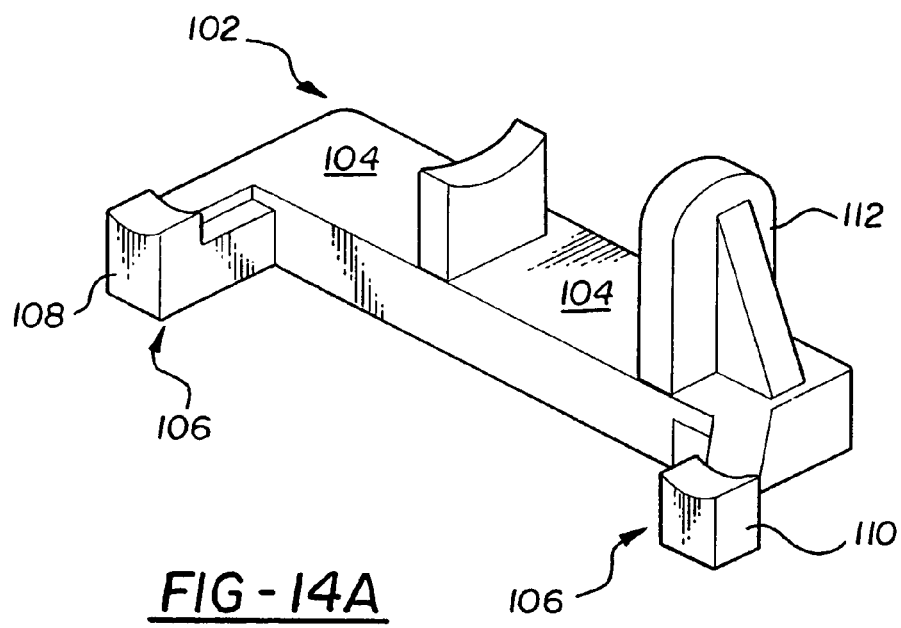
FIG. 14A is an enlarged perspective view of the actuator.
Figure 14B:
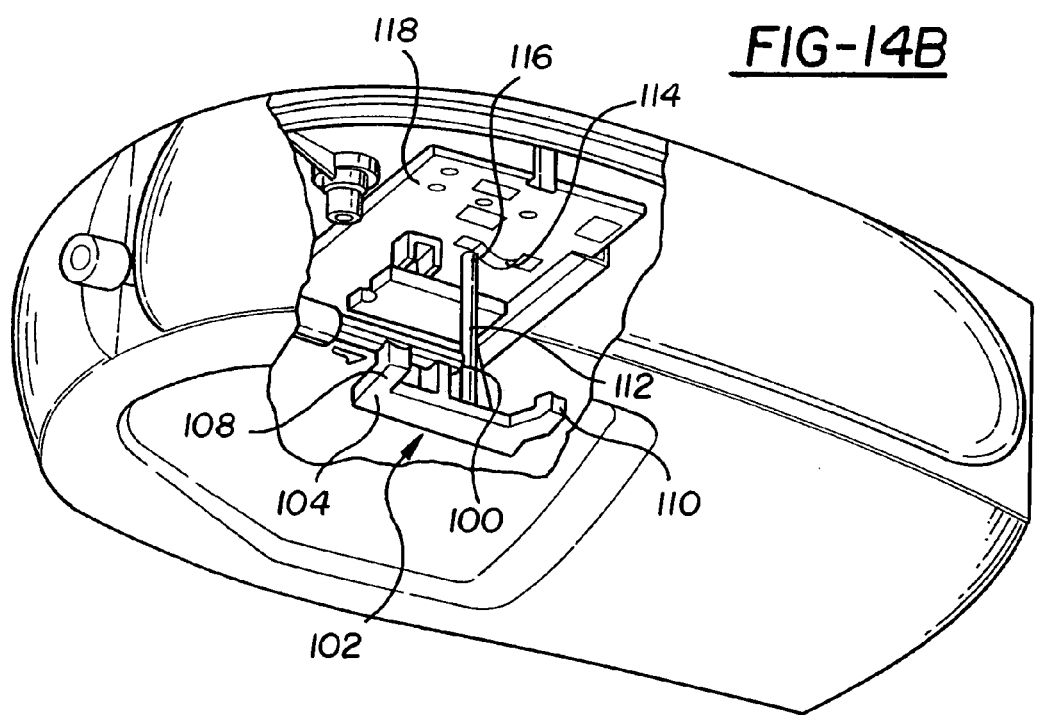
FIG. 14B is a perspective view of an alternative embodiment for the actuator including a control contact disposed at a distal end of an actuation arm.

Referring particularly to FIGS. 14A–14B, the actuator 102 is disclosed in greater detail. The actuator 102 includes a base portion 104 and at least one engagement arm 106 extending from the base portion 104. The at least one engagement arm 106 of the actuator 102 operatively engages the pump assembly 28 to retain the pump inlet 32 and the pump outlet 34 in the open state during sterilization. In the preferred embodiment of the subject invention, the actuator 102 more specifically includes first and second engagement arms 108, 110, respectively, extending from the base portion 104. In the preferred embodiment, the actuator 102 also includes an actuation arm 112. The actuation arm 112 extends from the base portion 104 between the first and second engagement arms 108, 110. As shown in the Figures, the actuation arm 112 extends upwardly from the base portion 104 between the first and second engagement arms 108, 110.

During sterilization, the first engagement arm 108 of the actuator 102 engages the first pinch lever 38 to move the first pinch lever 38 away from the pump inlet 32 to retain the pump inlet 32 in the open state. Similarly, during sterilization, the second engagement arm 110 of the actuator 102 engages the second pinch lever 40 to move the second pinch lever 40 away from the pump outlet 34 to retain the pump outlet 34 in the open state.

After sterilization it is desirable to move the actuator 102 into the disengaged position such that the pump assembly 28 can operate and the medication can be delivered to the patient 12. As indicated by the arrow (A) in FIG. 6D, the plunger 100 moves to displace the actuator 102 from the engaged position thereby moving the actuator 102 into the disengaged position. To displace the actuator 102, the plunger 100 engages the actuation arm 112. The plunger 100 displaces the actuator 102 from the operative engagement with the pump assembly 28 after sterilization such that the pump inlet 32 and the pump outlet 34 can alternate between the open and the closed state to deliver the medication to the patient 12. More specifically, the plunger 100 displaces the actuator 102 from the engagement with the first and second pinch levers 38, 40 after sterilization such that medication can be delivered to the patient 12. As such, the motor 42, which is operatively engaged to the first and second pinch levers 38, 40, can move these levers 38, 40 for drawing the medication into the pump housing 30 through the pump inlet 32 and for displacing the medication from the pump housing 30 through the pump outlet 34.

Referring now to FIG. 14B, a control contact 114, preferably a spring-like control contact 114, may be disposed at a distal end 116 of the actuation arm 112 away from the base portion 104 to indicate to the system 10 whether the actuator 102 is in the engaged or the disengaged position. The control contact 114 interacts with the actuation arm 112 of the actuator 102 upon the movement of the actuator 102 between the engaged or the disengaged position. If the control contact 114 is included, it is preferred that when the actuator 102 is disengaged from the first and second pinch levers 38, 40, i.e., when the actuator 102 is in the disengaged position, it contacts the control contact 114 to activate an electronic controller 118. The electronic controller 118 is activated to permit the pump assembly 28 to operate for delivering the medication to the patient 12. As indicated above, it is preferred that the actuation arm 112 of the actuator 102 is in contact with the control contact 114 when the actuator 102 is in the disengaged position. Of course, it is to be understood that the opposite could be true. That is, the system 10 can be designed such that the actuation arm 112 of the actuator 102 is in contact with the control contact 114 when the actuator 102 is in the engaged position.

The system 10 further includes a medication inlet tube 120 and a medication outlet tube 122. The medication inlet tube 120 is connected between the port 82 and the pump inlet 32 to provide access for the sterilization fluid to flow from the port 82 into the pump assembly 28, specifically into the pump inlet 32. The medication outlet tube 122 is connected between the pump outlet 34 and the port 82 to provide access for the sterilization fluid to flow from the pump assembly 28, specifically from the pump outlet 34, into the port 82. The medication inlet tube 120 and the first pinch lever 38 together establish the pump inlet 32, and the medication outlet tube 122 and the second pinch lever 40 together establish the pump outlet 34.

When the at least one biasing device 44 engages the first pinch lever 38 to normally-bias the first pinch lever 38 into the closed position, the medication inlet tube 120 is pinched. As such, the pump inlet 32 is maintained in the closed state. Similarly, when the at least one biasing device 44 engages the second pinch lever 40 to normally-bias the second pinch lever 40 into the closed position, the medication outlet tube 122 is pinched. As such, the pump outlet 34 is maintained in the closed state. However, as disclosed in FIG. 6D, when the actuator 102 is in the engaged position during sterilization, the actuator 42 overcomes the bias of the at least one biasing device 44 to move the first pinch lever 38 away from the medication inlet tube 120 such that the pump inlet 32 remains in the open state, and the actuator 102 overcomes the bias of the at least one biasing device 44 to move the second pinch lever 40 away from the medication outlet tube 122 such that the pump outlet 34 remains in the open state.

Referring particularly to FIGS. 3, and 8–10, the port 82 and the plunger 100 are described in greater detail. The plunger 100 includes a length L, a circumference C, and a plurality of seats 124 disposed along the length L and about the circumference C of the plunger 100. The seats 124 extend outwardly from the circumference C of the plunger 100 to the interior wall 90 of the elongated housing 84 of the port 82 to segregate the fluid chamber 92 of the elongated housing 84. A fluid passage, not numbered, is defined between each of the seats 124 and the interior wall 90 of the housing. These fluid passages control the flow of fluid within the port 82. Although the seats 124 may suitably segregate the fluid chamber 92, it is preferred that seals 126 are disposed about each of the seats 126 to assist with sealing the fluid passages from one another. In the most preferred embodiment, which is shown in the Figures, these seals are O-rings. At least one leak rib 128 extends at least partially along the interior wall 90 of the elongated housing 84. The at least one leak rib 128 selectively causes at least one of the seals 126 to leak when the plunger 100 is in the fill-position. As disclosed in the Figures, preferably there are two leak ribs 128 that extend along the interior wall 90 of the elongated housing 84.

As shown in FIGS. 11A–13B, the plunger 100 is at least partially hollow. As such, the plunger 100 defines an internal fluid bore 130 that extends within the plunger 100 between the seats 124. The plunger 100 further includes an access end 132 and a plunger actuation end 134. A plunger biasing device 136, preferably a compression spring, is disposed about the plunger actuation end 134 of the plunger 100 to bias the plunger 100 into the off-position. The internal fluid bore 130 extends from the access end 132, where the fluid flows into and from the internal fluid bore 130, toward the plunger actuation end 134. The internal fluid bore 130 includes a fluid duct 138 in fluid communication with one of the fluid passages such that the flow can flow into and from the internal fluid bore 130.

In the most preferred embodiment of the subject invention, the plurality of seats 124 are further defined as a first, second, third, and fourth seat 140, 142, 144, 146, respectively. The first seat 140 is disposed toward the access end 132 of the plunger 100, the fourth seat 146 is disposed toward the plunger actuation end 134 of the plunger 100, and the second and third seats 142, 144 are disposed successively between the first and fourth seats 140, 146. In this embodiment, the fluid passages are further defined as a first, second, and third fluid passage 148, 150, 152, respectively. The first fluid passage 148 is defined between the first and second seats 140, 142 and the interior wall 90, the second fluid passage 150 is defined between the second and third seats 142, 144 and the interior wall 90, and the third fluid passage 152 is defined between the third and fourth seats 144, 146 and the interior wall 90.

A first seal 154 is disposed about the first seat 140 for sealing the first fluid passage 148 from the access end 132 of the plunger 100, a second seal 156 is disposed about the second seat 142 for sealing the first and second fluid passages 148, 150 from one another, a third seal 158 is disposed about the third seat 144 for sealing the second and third fluid passages 150, 152 from one another, and a fourth seal 160 is disposed about the fourth seat 146 for sealing the third fluid passage 152 from the plunger actuation end 134 of the plunger 100. In this embodiment, the at least one leak rib 128 extends along the interior wall 90 of the elongated housing 84 from the proximate end 86 toward the distal end 88 just beyond the first seal 154 such that only the first seal 154 selectively leaks when the plunger 100 is in the fill-position.

In this most preferred embodiment, the internal fluid bore 130 extends within the plunger 100 from the access end 132 to the third seat 144. As such, the fluid duct 138 is in fluid communication with the second fluid passage 150 defined between the second and third seats 142, 144 and the interior wall 90 such that the fluid can flow into and from the internal fluid bore 130 at the second fluid passage 150.

The off-, fill-, and fluid delivery-positions of the plunger 100 are now described in the context of this most preferred embodiment having four seats 140, 142, 144, 146, three fluid passages 148, 150, 152, and four seals 154, 156, 158, 160. Referring to FIGS. 11A–11B, when the plunger 100 is in the off-position, the first, second, and third fluid connectors 94, 96, 98 are isolated from the proximate end 86 of the elongated housing 84 and from the access end 132 of the plunger 100 by the first, second, and third seats 140, 142, 144. In this off-position, the first and third fluid connectors 94, 98 are aligned with the third fluid passage 152.

Referring to FIGS. 12A–12B, when the plunger 100 is in the fill-position, the first and third fluid connectors 94, 98 are in fluid communication with the proximate end 86 of the elongated housing 84 and with the access end 132 of the plunger 100 through the second fluid passage 150 and the fluid duct 138 of the internal fluid bore 130. In this fill-position, the first and third fluid connectors 94, 98 are aligned with the second fluid passage 150. As such, the fluid can be filled through the access end 132 of the plunger 100, through the internal fluid bore 130 and the fluid duct 138, and into the reservoir 24 and the pump assembly 28. In the fill-position, the second fluid connector 96 is isolated from the proximate end 86 of the elongated housing 84, from the access end 132 of the plunger 100, and from the first and third fluid connectors 94, 98 by the third and fourth seats 144, 146.

Referring to FIGS. 13A–13B, when the plunger 100 is in the fluid delivery-position, the second fluid connector 96 is in fluid communication with the proximate end 86 of the housing and with the access end 132 of the plunger 100 through said second fluid passage 150 and the fluid duct 138 of the internal fluid bore 130. In the fluid delivery-position, the medication is delivered from the pump assembly 28 to the patient 12. In the fluid delivery-position, the first and third fluid connectors 94, 98 are isolated from the proximate end 86 of the housing and from the access end 132 of the plunger 100 by the first and second seats 140, 142. However, the first and third fluid connectors 94, 98 are in fluid communication with the reservoir 24 through the first fluid passage 148 to supply the pump assembly 28 with the fluid, i.e., with the medication. That is, in the fluid delivery-position, the first and third fluid connectors 94, 98 are aligned with the first fluid passage 148.

A fluid filling device, shown generally in FIG. 12B at 162, engages the proximate end 86 of the housing to automatically move the plunger 100 into the fill-position for filling the reservoir 24 and the pump assembly 28. If the system 10 is being sterilized, then the fluid filling device 162 is preferably a fluid, or sterilization, cap 164 (shown detached from the system 10 in FIG. 12B) that moves the plunger 100 into the fill-position to enable a sterilization fluid to penetrate into the reservoir 24 and the pump assembly 28. The fluid cap 164, by design, automatically moves the plunger 100 into the fill-position. Therefore, when the system 10 is introduced into a chamber filled with the sterilization fluid, preferably EtO gas, then the sterilization fluid flows, or seeps, through the fluid cap 164, through the proximate end 86 of the elongated housing 84 and the access end 132 of the plunger 100, through the internal fluid bore 130 and the fluid duct 138, into the second fluid passage 150, through the third fluid connector 98 into the reservoir 24, and through the first fluid connector 94 into the pump assembly 28.

If the system 10 is being filled with medication, then the fluid filling device 162 is preferably a syringe 166 that moves the plunger 100 into the fill-position for filling the reservoir 24 and the pump assembly 28. The syringe 166 (shown attached to the system 10 in FIG. 12B) engages the access end 132 of the plunger 100 and, by design, automatically moves the plunger 100 into the fill-position for filling the reservoir 24 and the pump assembly 28 through the internal fluid bore 130. Therefore, when the system 10 is being filled, the syringe 166 interacts with the proximate end 86 of the elongated housing 84 and the access end 132 of the plunger 100 and, as the syringe plunger is depressed, the medication flows through the internal fluid bore 130 and the fluid duct 138, into the second fluid passage 150, through the third fluid connector 98 into the reservoir 24, and through the first fluid connector 94 into the pump assembly 28.

To deliver the medication to the patient 12, the system 10 is utilized in combination with the infusion tube set 14. Referring back to FIG. 1A, the infusion tube set 14 includes a fluid end 168 and a patient end 170. The fluid end 168 of the tube set 14, through a delivery connector 172, engages the proximate end 86 of the elongated housing 84 and the access end 132 of the plunger 100 to automatically move the plunger 100 into the fluid delivery-position for delivering the medication to the patient 12. Therefore, as shown in FIGS. 13A–13B, when the pump assembly 28 is operating, the medication is drawn from the reservoir 24 through the third fluid connector 98 into the port 82 at the first fluid passage 148, and through the first fluid connector 94 into the pump inlet 32. The medication is then displaced out of the pump assembly 28 through the pump outlet 34, through the second fluid connector 96 into the port 82 at the second fluid passage 150, through the fluid duct 138 and the internal fluid bore 130 of the plunger 100, and out the access end 132 of the plunger 100 at the fluid end 168 of the infusion tube set 14. From there, the medication flows through the infusion tube set 14, out the patient end 170, and to the patient 12.

Referring back to FIG. 4, the system 10 further includes the electronic controller 118. The electronic controller 118 controls an amount of the medication that is to be delivered to the patient 12. The electronic controller 118 is mounted to the base housing 16, specifically to the top housing 22 of the base housing 16. Furthermore, the electronic controller 118 remains mounted to the base housing 16 during sterilization such that the entire system 10, including all mechanical components, the reservoir 24, and the electronic controller 118, is simultaneously sterilized. An electronic display 174 and at least one control button 176 are mounted to the base housing 16. The electronic display 174 and the control button 176 interact with the electronic controller 118 to control the amount of the medication to be delivered to the patient 12. As with the electronic controller 118, the electronic display 174 and the control button 176 also remain mounted to the base housing 16 during sterilization.

Figure 15A:
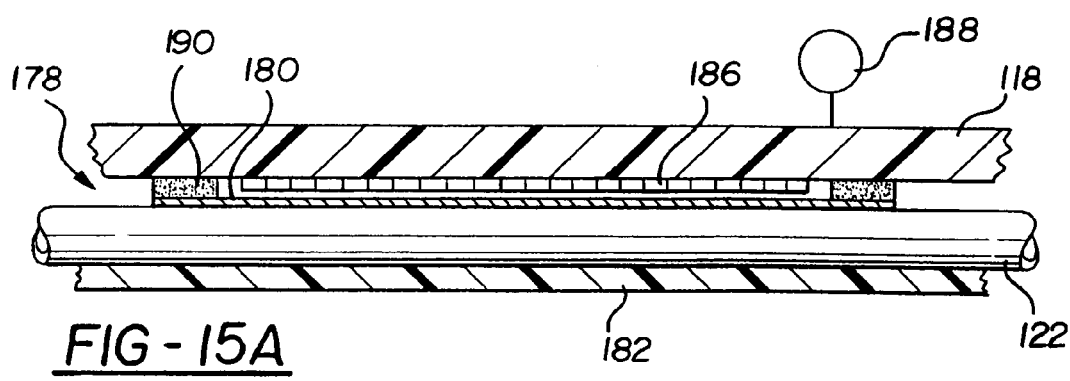
FIG. 15A is a partially cross-sectional side view of a blockage detection system according to the subject invention when the medication outlet tube is in a normal condition.
Figure 15B:
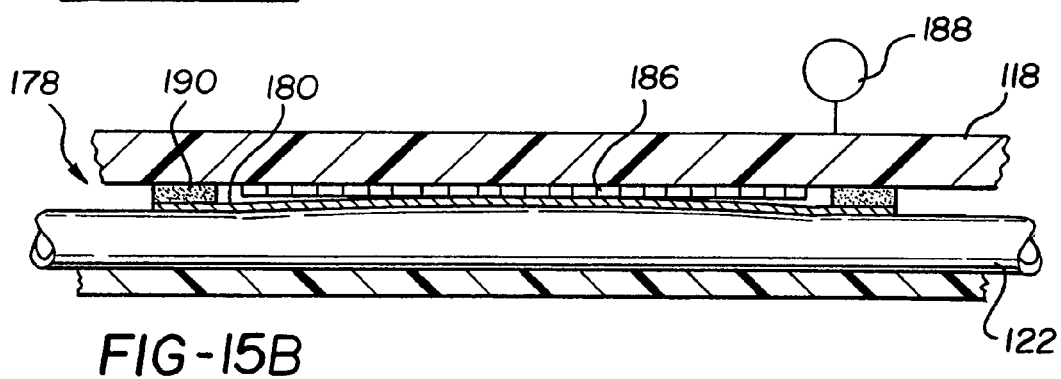
FIG. 15B is a partially cross-sectional side view of the blockage detection system of FIG. 15A when the medication outlet tube is in an expanded condition due to a blockage.

The subject invention also provides a blockage detection system which is generally disclosed at 178 in FIGS. 15A–15B. The blockage detection system 178 detects a blockage in the flow of the medication to the patient 12. The blockage detection system 178 comprises the base housing 16, the reservoir 24, the port 82, the pump assembly 28, the medication outlet tube 122, and the electronic controller 118. The blockage detection system 178 also includes a detection film 180 which is described below.

In the blockage detection system 178, the electronic controller 118 is mounted to the base housing 16 adjacent the outlet tube 122. The outlet tube 122 is mounted to the base housing 16 and, as described above, is connected between the pump assembly 28 and the port 82 to provide access for the medication to flow from the pump assembly 28 into the port 82 and to the patient 12. The outlet tube 122 has a diameter that is contractible and expandable between a normal condition (see FIG. 15A) and an expanded condition (see FIG. 15B). The diameter of the outlet tube 122 contracts and expands in response to variations in pressure that result from the flow of the medication from the reservoir 24 through the pump assembly 28 into the port 82 and to the patient 12.

As disclosed in the Figures, the outlet tube 122 is mounted to the base housing 16 via a support platform 182. That is, the support platform 182 is mounted on the base housing 16 to support the outlet tube 122 on the base housing 16. The support platform 182 includes at least one tube slot 184. The at least one tube slot 184 houses the diameter of the outlet tube 122. The outlet tube 122 is mounted in the tube slot 184 such that at least a portion, not numbered, of the diameter of the outlet tube 122 is exposed to the detection film 180.

The detection film 180 is disposed between the electronic controller 118 and the outlet tube 122. The detection film 180 is in contact with the outlet tube 122 and remains spaced from the electronic controller 118 when the diameter of the outlet tube 122 is in the normal condition, as in FIG. 15A. On the other hand, the detection film 180 is in contact with the outlet tube 122 and contacts the electronic controller 118 to activate the electronic controller 118 when the diameter of the outlet tube 122 is in the expanded condition, as in FIG. 15B, in response to increased pressure resulting from the blockage in the flow of the medication to the patient 12. More specifically, it is preferred that an electronic switch 186 is embedded in the electronic controller 118 between the electronic controller 118 and the detection film 180. The detection film 180 interacts with the electronic controller 118 by contacting the electronic switch 186 to activate the electronic controller 118 when the diameter of the outlet tube 122 is in the expanded condition.

For activating the electronic controller 118 when the diameter of the outlet tube 122 is in the expanded condition, it is also preferred that the detection film 180 is conductive. Once activated by the detection film 180, the electronic controller 118 deactivates the pump assembly 28 to prevent delivery of the medication to the patient 12 when the diameter of the outlet tube 122 is in the expanded condition. Deactivation of the pump assembly 28 prevents further blockage and further increases in pressure. To properly ensure that the there is a blockage in the outlet tube 122, it is most preferred that the electronic controller 118, and therefore the pump assembly 28, are deactivated only if the diameter of the outlet tube 122 is in the expanded condition for more than at least one cycle of the pump assembly 28. This additional measure avoids false readings and the deactivation of the pump assembly 28 when the outlet tube 122 is truly not blocked.

Additionally, once activated by the detection film 180, the electronic controller 118 may also activate an alarm 188, shown schematically in the Figures. The alarm 188, which can be audible and/or visually displayed on the electronic display 174, would indicate the blockage that is due to the blockage in the flow of the medication to the patient 12.

It is preferred that the detection film 180 is mounted to the electronic controller 118. Although the detection film 180 is mounted to the electronic controller 118, a portion, not numbered, of the detection film 180 remains at least partially-spaced from the electronic controller 118 when the diameter of the outlet tube 122 is in the normal condition. The detection film 180 is mounted to the electronic controller 118 with an adhesive layer 190. The adhesive layer 190 also establishes a thickness that is necessary to space the detection film 180, specifically the portion of the detection film 180, from the electronic controller 118 when the diameter of the outlet tube 122 is in the normal condition. The portion of the detection film 180 contacts the electronic controller 118 to activate the electronic controller 118 when the diameter of the outlet tube 122 is in the expanded condition in response to increased pressure in the outlet tube 122.

Figure 17:
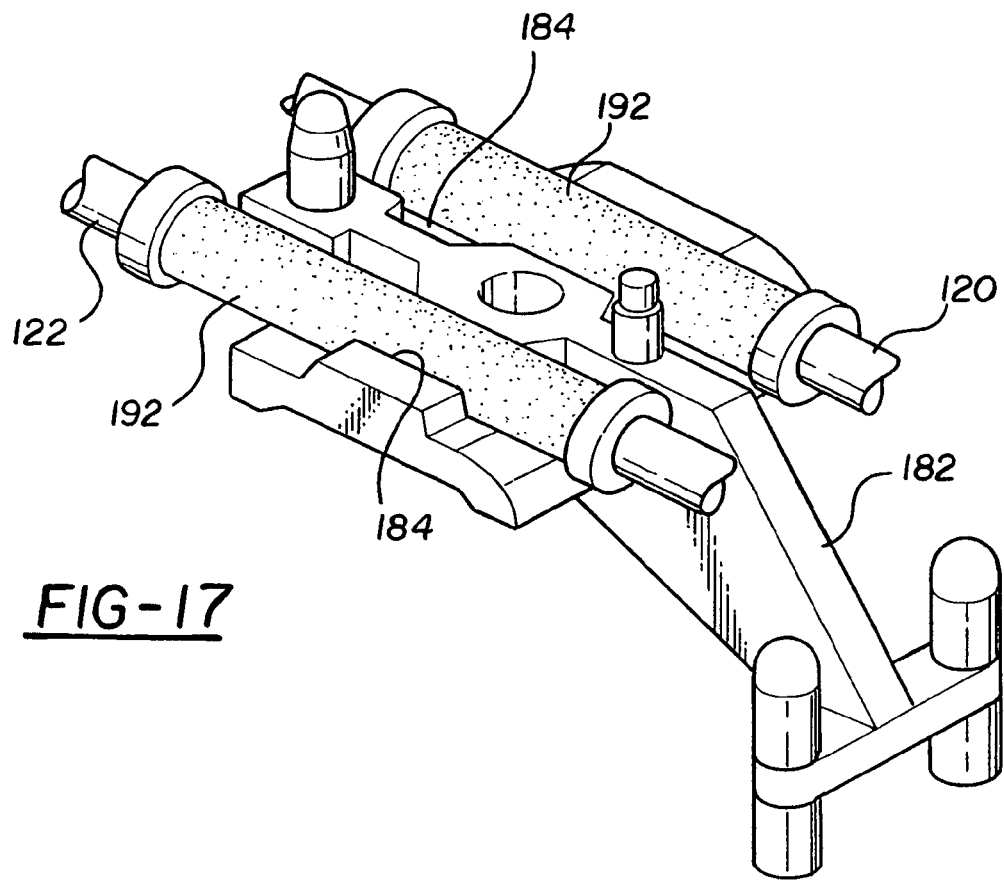
FIG. 17 is a perspective view of a support platform with the medication inlet and outlet tubes which also illustrates alternative embodiments for the blockage detection system and the empty detection system where a coating is applied to the medication inlet and outlet tubes.

An alternative embodiment for the blockage detection system 178 is disclosed in FIG. 17. In this alternative embodiment, the detection film 180 is eliminated, and a coating 192 is included. The coating 192 is applied to the outlet tube 122. The coating 192 activates the electronic controller 118 when the diameter of the outlet tube 122 is in the expanded condition in response to increased pressure resulting from the blockage in the flow of the medication to the patient 12. As with the detection film 180, the coating 192 is preferably conductive. If the coating 192 is present, it is most preferred that the coating 192 is formed of conductive carbon. However, other coatings may be used that impart conductive properties to the coating 192.

For the most part, the other characteristics of this alternative embodiment for the blockage detection system 178 are identical to the characteristics that were described above in the preferred embodiment for the blockage detection system 178. Notably, the outlet tube 122 is mounted in the tube slot 184 in this alternative embodiment such that at least a portion of the coating 192 is exposed beyond the tube slot 184.

Figure 16A:
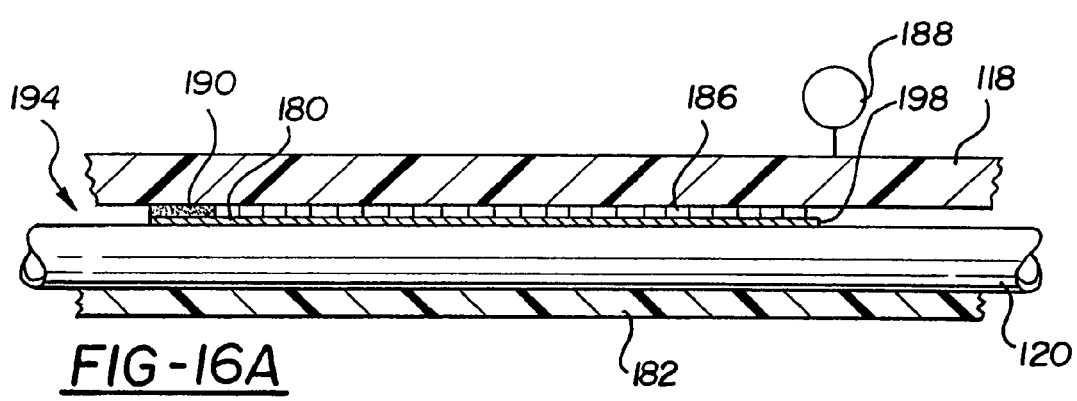
FIG. 16A is a partially cross-sectional side view of an empty detection system according to the subject invention when the medication inlet tube is in a normal condition.
Figure 16B:
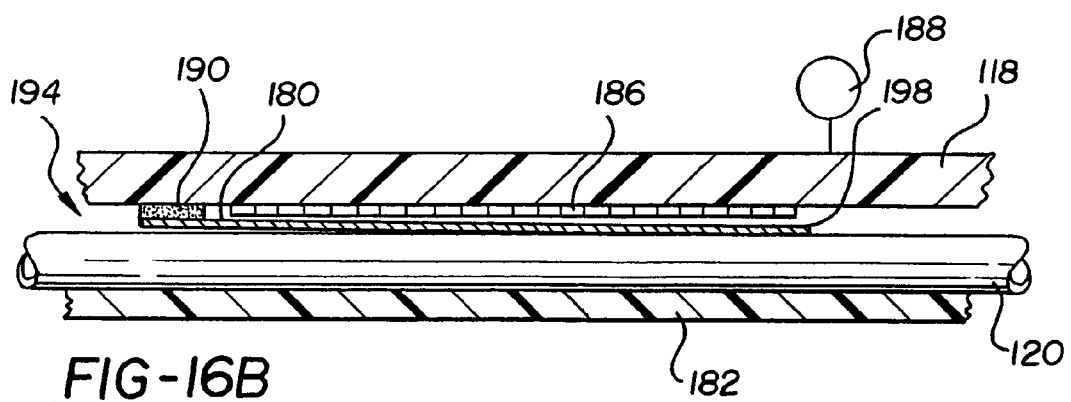
FIG. 16B is a partially cross-sectional side view of the empty detection system of FIG. 16A when the medication inlet tube is in a collapsed condition due to a depletion in the supply of the medication.

The subject invention also provides an empty detection system which is generally disclosed at 194 in FIGS. 16A–16B. The empty detection system 194 determines when a supply of the medication has been depleted. The empty detection system 194 comprises the base housing 16, the reservoir 24 for storing the supply of the medication to be delivered to the patient 12, the port 82, the pump assembly 28, the medication inlet tube 120, and the electronic controller 118. As with the blockage detection system 178, the preferred embodiment of the empty detection system 194 also includes a detection film, also numbered 180, which is described below.

In the empty detection system 194, the electronic controller 118 is mounted to the base housing 16 adjacent the inlet tube 120. The inlet tube 120 is mounted to the base housing 16 and, as described above, is connected between the reservoir 24 and the pump assembly 28 to provide access for the medication to flow from the reservoir 24 into the pump assembly 28 and to the patient 12. The inlet tube 120 has a diameter that is contractible and expandable between a normal condition (see FIG. 16A) and a collapsed condition (see FIG. 16B). The inlet tube 120 contracts into the collapsed condition and expands from the collapsed condition into the normal condition. The diameter of the inlet tube 120 contracts and expands in response to variations in pressure that result from a lack of the flow of the medication from the reservoir 24 through the pump assembly 28 and to the patient 12.

As disclosed in the Figures, the inlet tube 120 is mounted to the base housing 16 via the support platform 182. That is, the support platform 182 is mounted on the base housing 16 to support the inlet tube 120 on the base housing 16. The support platform 182 includes the at least one tube slot 184. The at least one tube slot 184 houses the diameter of the inlet tube 120. The inlet tube 120 is mounted in the tube slot 184 such that at least a portion of the diameter of the inlet tube 120 is exposed to the detection film 180.

The detection film 180 is disposed between the electronic controller 118 and the inlet tube 120. As shown in FIG. 16A, the detection film 180 is in contact with the inlet tube 120 and contacts the electronic controller 118 to activate the electronic controller 118 when the diameter of the inlet tube 120 is in the normal condition. On the other hand, as shown in FIG. 16B, the detection film 180 becomes spaced from the electronic controller 118 to deactivate the electronic controller 118 when the diameter of the inlet tube 120 is in the collapsed condition in response to the lack of flow of the medication that results from the supply of the medication being depleted.

It is preferred that an electronic switch 186 is embedded in the electronic controller 118 between the electronic controller 118 and the detection film 180. The detection film 180 contacts the electronic switch 186 to activate the electronic controller 118 when the diameter of the inlet tube 120 is in the normal condition, and the detection film 180 becomes spaced from the electronic switch 186 to deactivate the electronic controller 118 when the diameter of the inlet tube 120 is in the collapsed condition.

Figure 4:
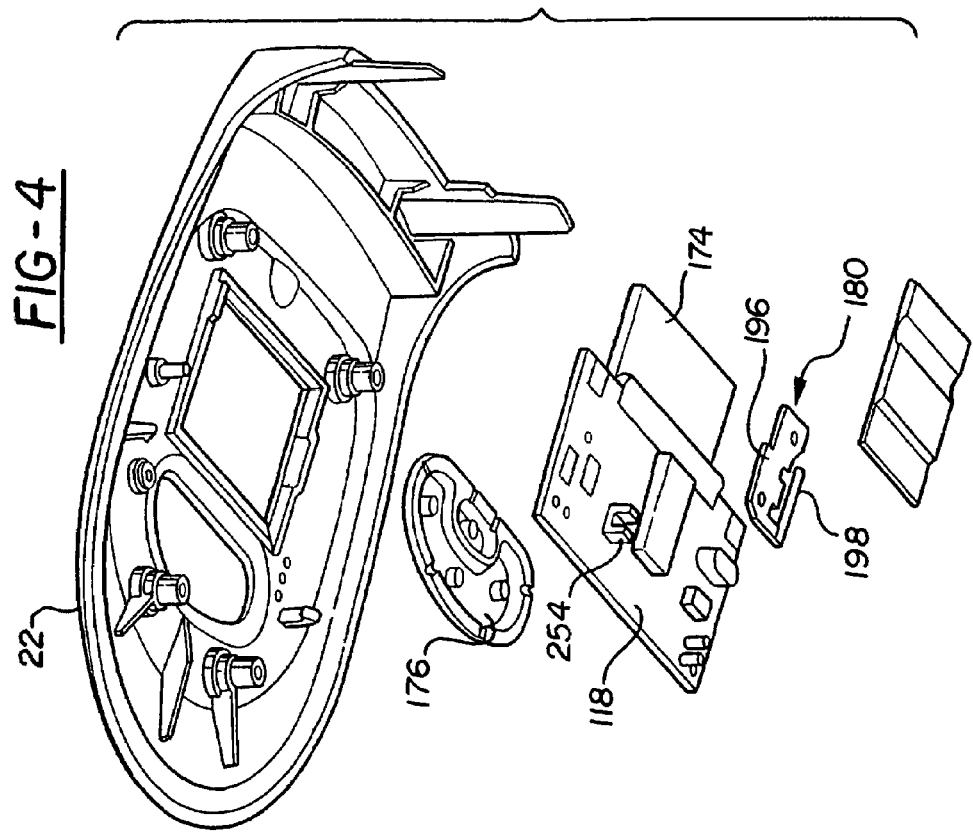
FIG. 4 is an exploded perspective view of the system illustrating an underside of the top housing, at least one control button, an electronic controller and display, and a detection film having a cantilever portion.

As best disclosed in FIG. 4, the detection film 180 more specifically includes a film base portion 196 and a cantilever portion 198. The film base portion 196 of the detection film 180 is mounted to the electronic controller 118 away from the electronic switch 186, and the cantilever portion 198 of the detection film 180 is adjacent the electronic switch 186. More specifically, the cantilever portion 198 extends from the film base portion 104 to contact the electronic switch 186 when the diameter of the inlet tube 120 is in the normal condition. It is the cantilever portion 198 of the detection film 180 that becomes spaced from the electronic controller 118 to deactivate the electronic controller 118 when the diameter of the inlet tube 120 is in the collapsed condition. For activating the electronic controller 118 when the diameter of the inlet tube 120 is in the normal condition, it is also preferred that the detection film 180, specifically the cantilever portion 198 of the detection film 180, is conductive. Preferably, the detection film 180 is mounted to the electronic controller 118 with an adhesive layer 190. Of course, it is the film base portion 196 of the detection film 180 that is directly mounted to the electronic controller 118. The cantilever portion 198 of the detection film 180 is not directly mounted, or otherwise adhered, to the electronic controller 118 such that this portion of the detection film 180 can become spaced from the electronic controller 118 when the diameter of the inlet tube 120 is in the collapsed condition.

Once the detection film 180 becomes spaced from the electronic controller 118, i.e., when the diameter of the inlet tube 120 is in the collapsed condition, the portion of the electronic controller 118 that interacts with the pump assembly 28 is deactivated such that the pump assembly 28 is deactivated. Deactivation of the pump assembly 28 after it has been determined that the supply of the medication has been depleted prevents a build up of air in the system. To properly ensure that the supply of the medication has been depleted, it is most preferred that the electronic controller 118, and therefore the pump assembly 28, are deactivated only if the diameter of the inlet tube 120 is in the collapsed condition for more than at least one cycle of the pump assembly 28. This additional measure avoids false readings and the deactivation of the pump assembly 28 when the supply of the medication is truly not depleted.

Additionally, deactivation of the portion of the electronic controller 118 that interacts with the pump assembly 28 may also cause the electronic controller 118 to activate the alarm 188. The alarm 188, which can be audible and/or visually displayed on the electronic display 174, would indicate the lack of flow of the medication when the diameter of the inlet tube 120 is in the collapsed condition due to the lack of flow of the medication to the patient 12.

An alternative embodiment for the empty detection system 194 is disclosed in FIG. 17. In this alternative embodiment, the detection film 180 is eliminated, and the coating 192 is included. The coating 192 is applied to the inlet tube 120. The coating 192 contacts the electronic controller 118 to activate the electronic controller 118 when the diameter of the inlet tube 120 is in the normal condition. On the other hand, the coating 192 becomes spaced from the electronic controller 118 to deactivate the electronic controller 118 when the diameter of the inlet tube 120 is in the collapsed condition in response to the lack of flow of the medication resulting from the supply of the medication being depleted. As with the detection film 180, the coating 192 is preferably conductive. If the coating 192 is present, it is most preferred that the coating 192 is formed of conductive carbon. However, other coatings may be used that impart conductive properties to the coating 192.

For the most part, the other characteristics of this alternative embodiment for the empty detection system 194 are identical to the characteristics that were described above in the preferred embodiment for the empty detection system 194. Notably, the inlet tube 120 is mounted in the tube slot 184 in this alternative embodiment such that at least a portion of the coating 192 is exposed beyond the tube slot 184.

Referring now to FIGS. 1B, 6A–6D, and 18A–18B, the system 10 of the subject invention can be tested using a testing instrument 200 after assembly of the system 10. The system 10 is tested after assembly and prior to shipment and use by the surgeons, patients, and the like to confirm various operations of the system 10. In the preferred embodiment, to test the system 10, the system 10 is mounted onto the testing instrument 200. One operation of the system 10 that is confirmed after assembly of the system 10 is the operation of the pump assembly 28.

To confirm these operations, the system 10 includes at least one testing access port 202. The at least one testing access port 202 is defined within the base housing 16 and is aligned with at least one of the pump inlet 32, the pump outlet 34, and the actuator 102. Preferably, the at least one testing access port 202 is aligned with all three of the pump inlet 32, the pump outlet 34, and the actuator 102. The at least one testing access port 202 provides access for the testing instrument 200 to move the actuator 102 between the disengaged position and the engaged position. If the at least one testing access port 202 is aligned with the pump inlet 32 and the pump outlet 34 then it is aligned with the first and second pinch levers 38, 40, respectively. Also, as for the alignment with the actuator 102, the at least one testing access port 202 is more specifically aligned with the at least one engagement arm 106 of the actuator 102. This provides access for the testing instrument 200 to move the actuator 102 between the disengaged position and the engaged position.

The system 10 is preferably assembled with the actuator 102 in the engaged position such that the first and second pinch levers 38, 40 are in the open position and the resiliency and life of the medication inlet and outlet tubes 120, 122 is not compromised. Because the at least one testing access port 202 provides access for the testing instrument 200 to move the actuator 102 between the disengaged position and the engaged position, the testing instrument 200 can be inserted into the at least one testing access port 202 to disengage the actuator 102, i.e., to move the actuator 102 into the disengaged position. As such, the pump inlet 32 and the pump outlet 34 can alternate between the open and closed states after assembly and during testing of the system 10.

The at least one testing access port also provides access for the testing instrument 200 such that the pump inlet 32 and the pump outlet 34 can be retained in the open state after the system 10 has been tested to prepare the system 10 for sterilization. That is, after the system 10 has been tested, the actuator 102 is moved from the disengaged position back into the engaged position to prepare the system 10 for sterilization. In the engaged position, the first and second pinch levers 38, 40 are retained in the open state.

In the preferred embodiment, the at least one testing access port 202 is further defined as first, second, and third testing access ports 204, 206, 208, respectively. The first testing access port 204 is aligned with the pump inlet 32, the second testing access port 206 is aligned with the pump outlet 34, and the third testing access port 208 is aligned with the actuator 102 for providing access to the testing instrument 200 to move the actuator 102 into the engaged position. More specifically, the first testing access port 204 is aligned with the first pinch lever 38 such that the first pinch lever 38 is engaged by the testing instrument 200. Once inside the first testing access port 204, the testing instrument 200 forces the first pinch lever 38 away from the pump inlet 32 and forces the pump inlet 32 into the open state. Similarly, the second testing access port 206 is aligned with the second pinch lever 40 such that the second pinch lever 40 is engaged by the testing instrument 200. Once inside the second testing access port 206, the testing instrument 200 forces the second pinch lever 40 away from the pump outlet 34 and forces the pump outlet 34 into the open state. The first and second pinch levers 38, 40 include the lever guides 78 opposite the cam follower 76 of each pinch lever 38, 40. To move the first and second pinch levers 38, 40, the testing instrument 200 engages the lever guides 78 upon insertion into the first and second testing access ports 204, 206. After the testing instrument 200 forces the first and second pinch levers 38, 40 away from the pump inlet 32 and the pump outlet 34, respectively, the testing instrument 200 is introduced into the third testing access port 208 and the actuator 102 is moved into the engaged position to engage and retain the pinch levers 38, 40 in the open position such that the system 10 is now prepared for sterilization. It is to be understood by those skilled in the art that the testing instrument 200 includes male prongs, generally indicated at 210, that are introduced into the testing access ports 204, 206, 208.

The system 10 further includes at least one controller access port 212 defined within the base housing 16. In the preferred embodiment, the at least one controller access port 212 is defined within the top housing 22 or cover. The at least one controller access port 212 is aligned with the electronic controller 118 to provide access for a second testing instrument 214. It is to be understood that the second testing instrument 214 and the testing instrument 200 may be a unitary component, as disclosed in the Figures. The second testing instrument 214 causes the electronic controller 118 to activate the motor 42 such that the motor 42 is powered to alternate the pump inlet 32 and the pump outlet 34 between the open and closed states after assembly and during testing of the system 10. The second testing instrument 214 also preferably includes male prongs 210 that are introduced into the controller access ports 212.

Referring primarily to FIGS. 2A–3, and 19–20, the system 10 of the subject invention is also suitable to be carried by the patient 12. To facilitate carrying of the system 10 so the patient 12 can remain ambulatory, a carrying strap 216 is mounted within the base housing 16 for the carrying of the system 10 by the patient 12. An integral storage cavity 218 is defined within the base housing 16. The carrying strap 216 is at least partially disposed in the integral storage cavity 218. The carrying strap 216 at least partially extends from the integral storage cavity 218 to interact with the patient 12 for carrying the system 10.

Figure 20:
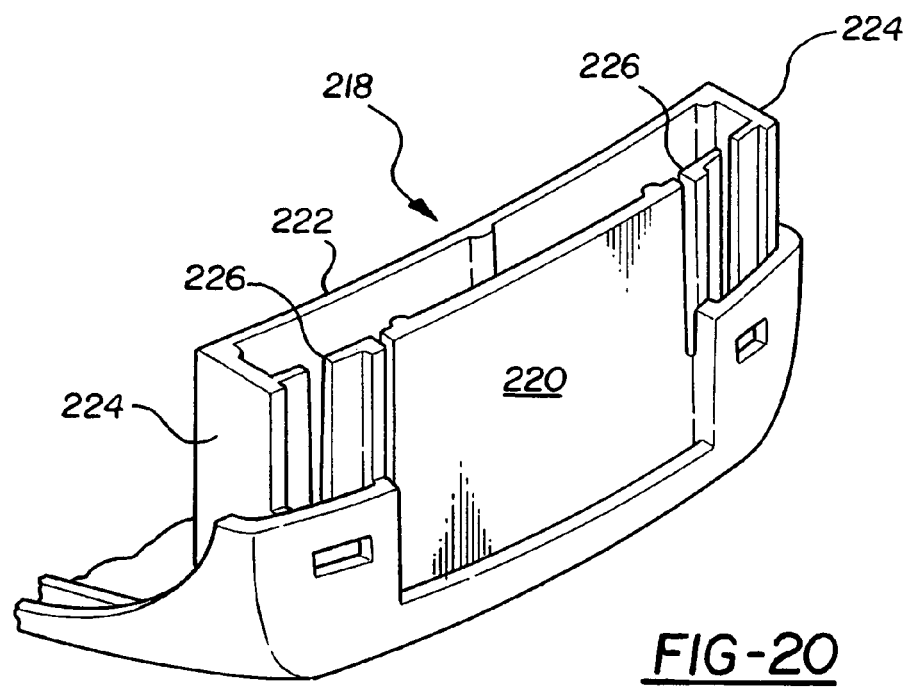
FIG. 20 is an enlarged top perspective view of the integral storage cavity defined within the base housing of the system.

The system 10 further includes a plurality of cavity walls. The cavity walls extend from the bottom housing 18 to define the integral storage cavity 218 between the bottom 18 and top 22 housings. Referring particularly to FIG. 20, the cavity walls are further defined as a front wall 220, a rear wall 222, and first and second side walls 224 extending between the front and rear walls 220, 222 to support the front and rear walls 220, 222 and to define the integral storage cavity 218. At least one strap slot 226 is defined within the front wall 220 such that at least a portion, not numbered, of the carrying strap 216 extends from the integral storage cavity 218 and through the strap slot 226. The patient 12 can then access the portion of the carrying strap 216 when desired.

In interacting with the carrying strap 216, the patient 12 simply manipulates, or grabs, the portion of the carrying strap 216 to pull a length of the carrying strap 216 from the integral storage cavity 218. This length is then looped about the head of the patient 12 as specifically disclosed in FIG. 19. In the preferred embodiment, the carrying strap 216 is retractable into the integral storage cavity 218 after the length has been pulled from the integral storage cavity 218 by the patient 12. The system 10 further includes a clip 228 that connects opposing ends of the carrying strap 216 such that the carrying strap 216 is adjustable to fit patients 12 of all sizes. In the most preferred embodiment of the subject invention, which is disclosed in FIG. 19, the carrying strap 216 is further defined as a shoulder strap. The shoulder strap suspends from a shoulder of the patient 12 for carrying the system 10.

Also, as particularly disclosed in FIG. 1B, the system 10 may also further include a system mounting clip 230 that extends from an exterior facing 232 of the base housing 16. The system mounting clip 230 can be mounted to a belt 234 of the patient 12. Of course, it is to be understood that the system mounting clip 230 is not to be limited to a clip for a belt 234. Instead, the system mounting clip 230 may be mounted to a shirt, a pocket, and the like.

Referring to FIGS. 2B, and 21–24, the subject invention further provides a method of controlling the system 10. This method is designed to be convenient for both the surgeon, or other medical professional, and the patient 12. A patient label 236, having a second set of explanatory indicia, i.e., instructions, is mounted, preferably adhered, to the system 10. A removable overlay label 238, having a first set of explanatory indicia, i.e., instructions, is mounted, preferably adhered, to the patient label 236 to at least partially cover the patient label 236.

The method includes the steps of selecting the amount of the medication in accordance with the first set of explanatory indicia on the removable overlay label 238. The medical professional selects the amount of the medication. As such, the first set of explanatory indicia is intended to be readily understood by the medical professional. Typically, the amount of the medication is selected by selecting the flow rate for the medication. Other parameters including, but not limited to, the bolus amount, the drug or medication concentration, and like, can also be selected.

Throughout the step of selecting, the medical professional and/or patient 12 interfaces with the electronic display 174 to view his or her selections. More specifically, the electronic display 174 presents a readable output for the medical professional and the patient 12. The readable output displayed on the electronic display 174 is correlated with the removable overlay label 238 and the patient label 236. That is, the readable output is correlated to the first and second sets of instructions. A first readable output is presented on the electronic display 174. The first readable output is linked with the first set of explanatory indicia when the removable overlay label 238 is displayed. Similarly, a second readable output is presented on the electronic display 174. The second readable output is linked with the second set of explanatory indicia after the system 10 has been locked. Locking the system 10 is described immediately below.

After the amount of the medication has been selected, the system 10 is locked such that selected amount of the medication to be delivered to the patient 12 is unable to be modified. After the medical professional is satisfied with his or her selection, the medical professional depresses the "LOCK" portion of the first set of explanatory indicia on the removable overlay label 238 to lock the system 10.

Figure 21:
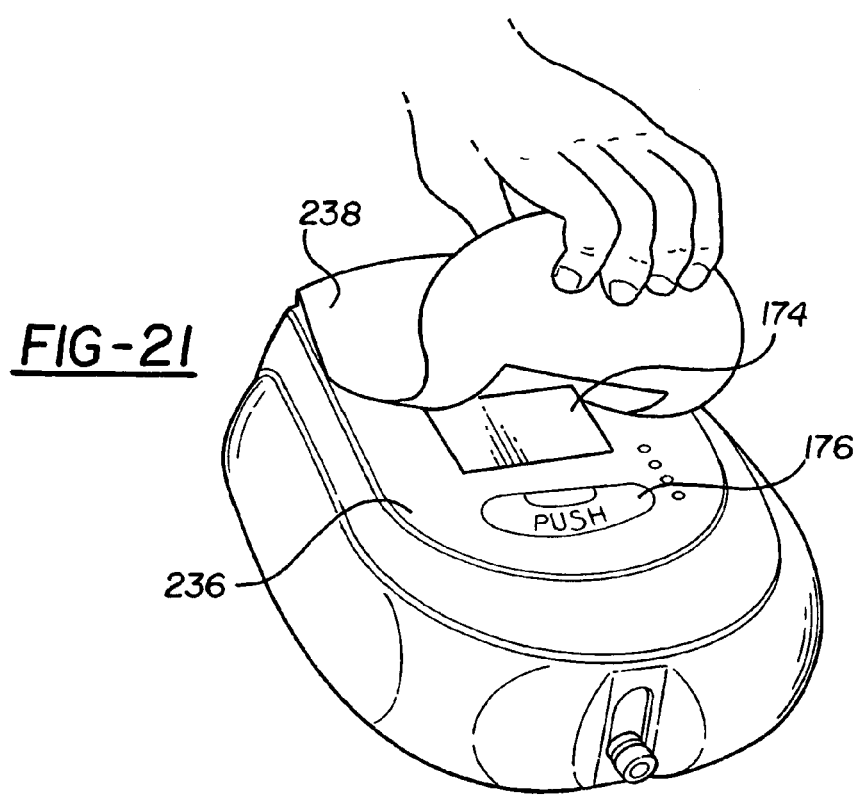
FIG. 21 is a perspective view of a surgeon or patient removing the removable overlay label to reveal the patient label.
Figure 22:
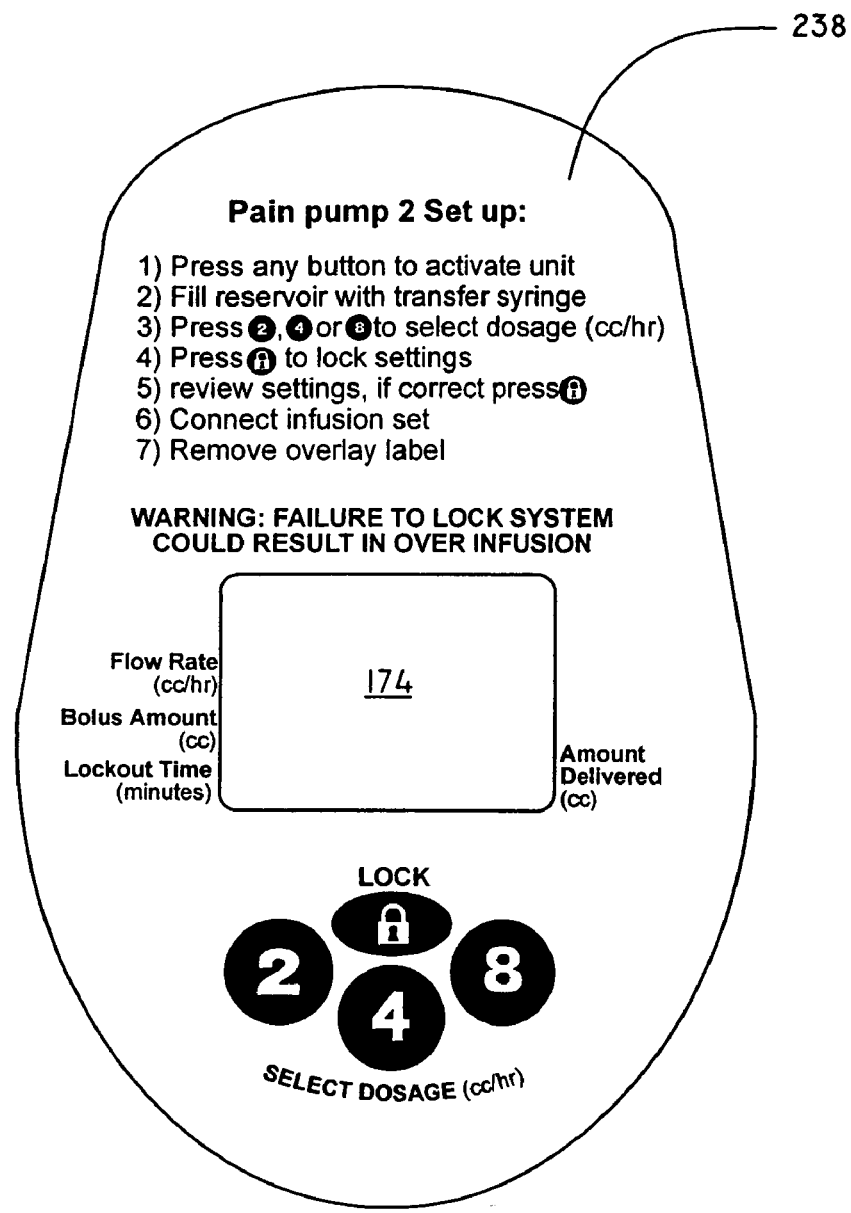
FIG. 22 is a plan view of one embodiment of the removable overlay label having a one version of a first set of explanatory indicia.
Figure 23:
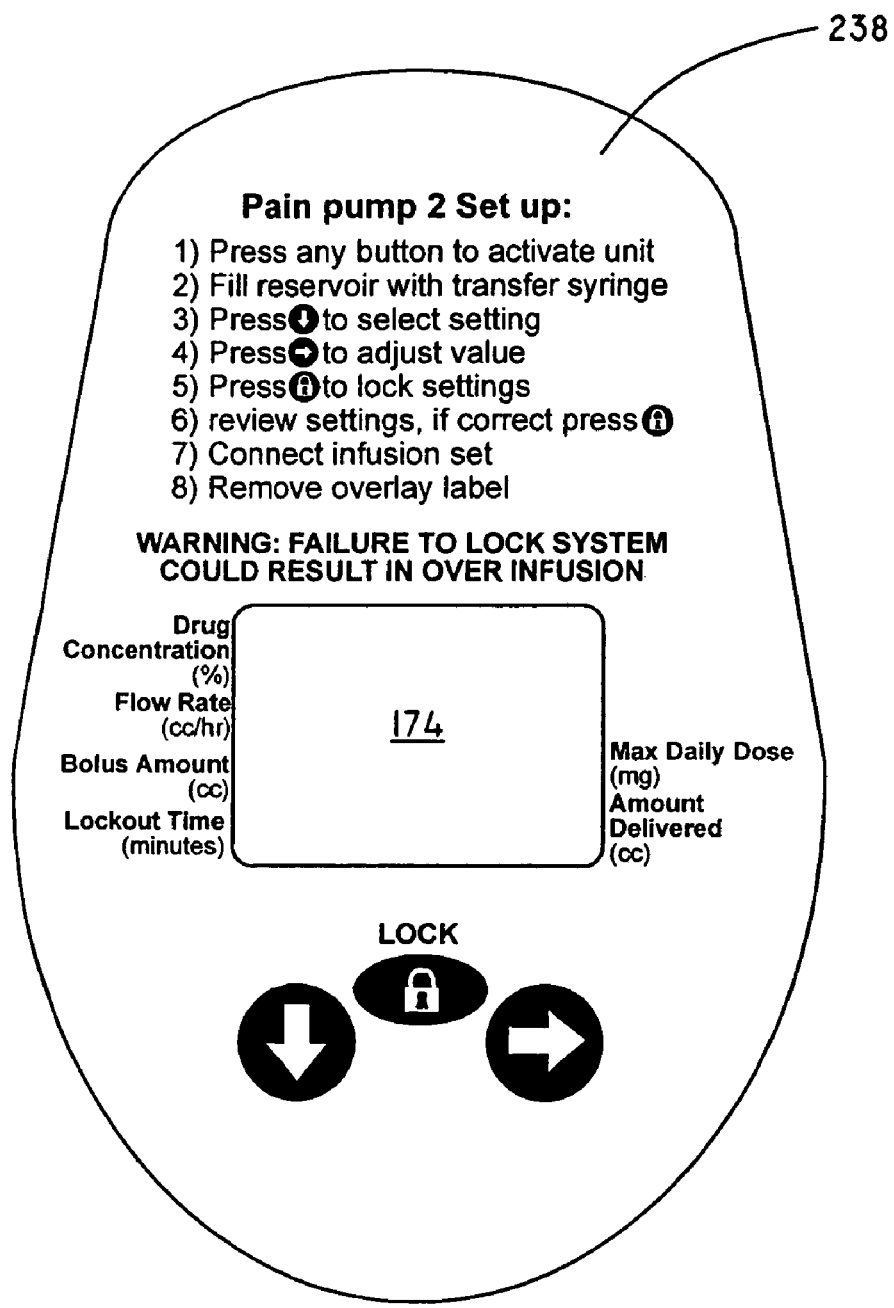
FIG. 23 is a plan view of a further embodiment of the removable overlay label having another version of a first set of explanatory indicia.
Figure 24:
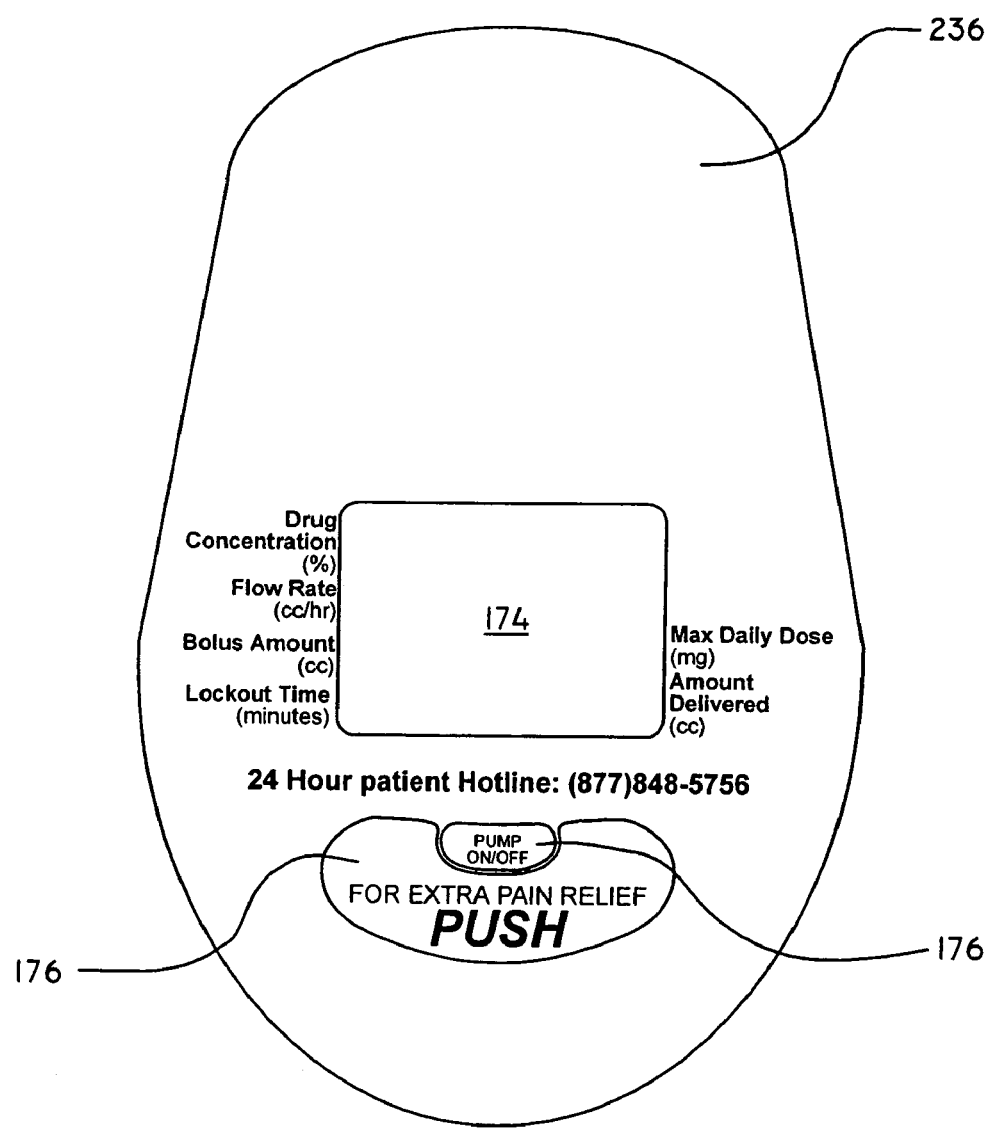
FIG. 24 is a plan view of the patient label having a second set of explanatory indicia.

Once the system 10 is locked, either the medical professional or the patient 12 can remove the removable overlay label 238 to reveal the patient label 236 (as shown in FIG. 21). To accomplish this, the user, either the medical professional or the patient 12, simply pulls the removable overlay label 238 off the patient label 236. This reveals the control button 176 that was originally masked under the removable overlay label 238. The system 10 is then operated in accordance with a second set of explanatory indicia on the patient label 236. The second set of explanatory indicia is intended to be readily understood by the patient 12. Once the system 10 is locked, the system 10 is designed to be convenient for use by the patient 12.

Upon locking the system 10, a functionality of the control button 176 is modified. As such, the functionality of the control button 176 is different when the removable overlay label 238 is displayed on the system 10 as compared to when the patient label 236 is displayed on the system 10. In other words, the functionality of the control button 176 is different when the medical professional interacts with the system 10 via the removable overlay label 238 as compared to when the patient 12 interacts with the system 10 via the patient label 236. When the removable overlay label 238 is displayed on the system 10, the control button 176 is at least tri-functional. On the other hand, after the system 10 has been locked and the patient label 236 is displayed on the system 10, the functionality of the control button 176 is converted from being at least tri-functional to being bi-functional.

In operating the system 10, the system 10 may be deactivated, if necessary, to stop delivery of the medication to the patient 12. To deactivate the system 10, the patient 12 depresses the "ON/OFF" portion of the, now bi-functional, control button 176 in response to the second set of explanatory indicia on the patient label 236. If the system 10 is deactivated, then the patient 12 may also use the control button 176 to activate the system 10 to re-start delivery of the medication to the patient 12. To accomplish this, the patient 12 depresses the "ON/OFF" portion of the control button 176 again.

Alternatively, in operating the system 10, the patient 12 may request an additional amount of the medication relative to the selected amount of the medication, and provided the Bolus amount will not be violated, the patient 12 will receive an additional amount of the medication. To request an additional amount of the medication relative to the selected amount, the patient 12 actuates the control button 176.

Figure 25:
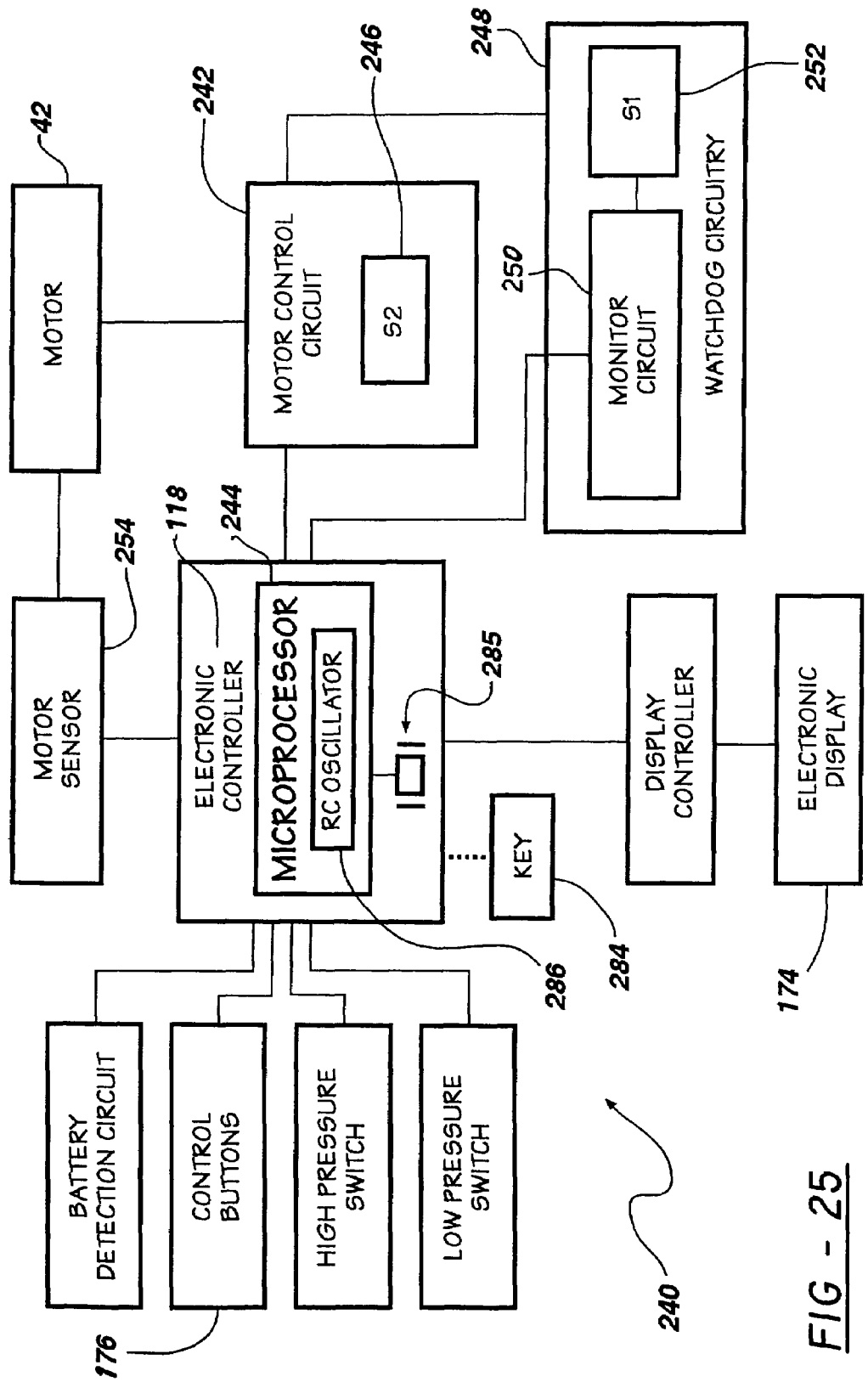
FIG. 25 is a block diagram schematically illustrating a control system for the integrated medication delivery system of the subject invention.

With specific reference to FIG. 25, a control system 240 for the system 10, according to an embodiment of the present invention is shown. The control system 240 includes the electronic controller 118 and a motor control circuit 242. The electronic controller 118 controls operation of the system 10 as described above.

In one embodiment, the electronic controller 118 includes a microprocessor 244. One suitable microprocessor 244 is available from Philips Semiconductor of Sunnyvale, Calif. as model no. 87LPC764. The electronic controller 118 is programmed to control operation of the motor control circuit 242 with a computer software program. In general, the electronic controller 118 generates control signals in accordance with the computer software program and delivers the control signals to the motor control circuit 242.

The motor control circuit 242 includes a first switch 246. The first switch 246 has an open state and a closed state.

The control system 240 also includes a watchdog circuit 248 coupled to the electronic controller 118. The watchdog circuit 248 includes a monitor circuit 250 and a second switch 252. The second switch 252 has an open state and a closed state and is coupled to the first switch 246. The monitor circuit 250 is adapted to detect an abnormal condition of the control system 240 and to turn the second switch 252 off if the abnormal condition is detected. Examples of an abnormal condition include, but are not limited to, too many revolutions of the motor 42, failure of the electronic controller 118, failure of the first switch 246, or failure of a motor sensor 254 (see below).

The motor control circuit 242 is adapted to receive control signals from the electronic controller 118 and to responsively supply power to the motor 42 by placing the first switch 246 in the closed state. Power is supplied to the motor 42 if the first and second switches 246, 252 are in the closed state.

Figure 26:
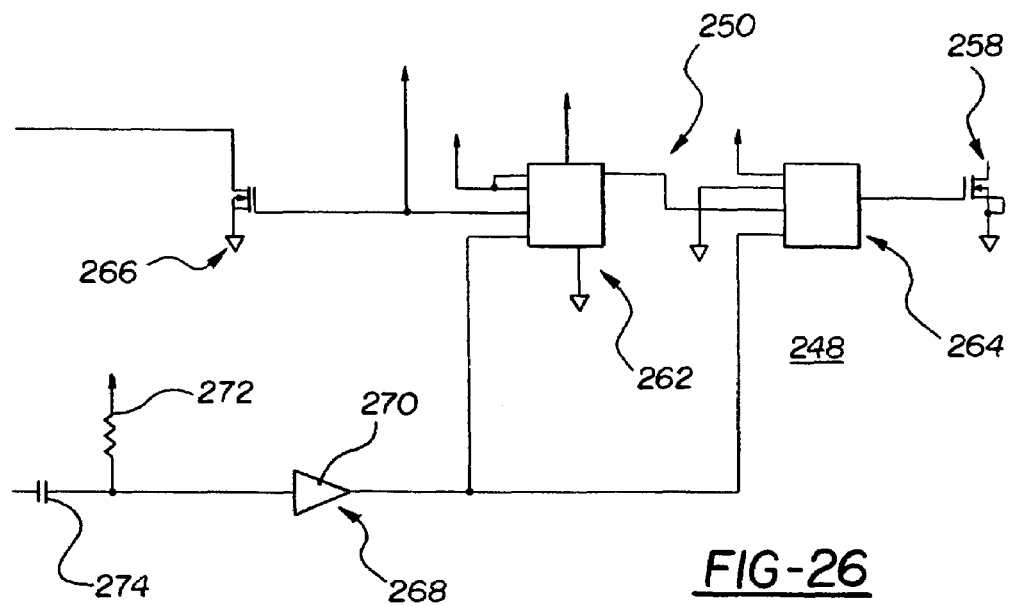
FIG. 26 is an electrical diagram illustrating portions of a watchdog circuit of the control system.
Figure 27:
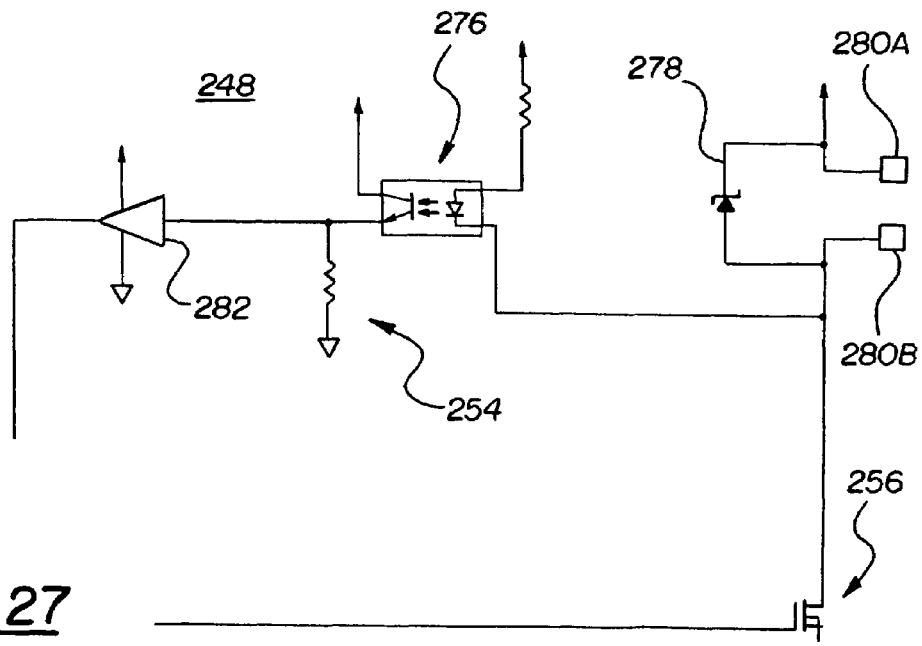
FIG. 27 is an electrical diagram illustrating further portions of the watchdog circuit of the control system.

With reference to FIGS. 26 and 27, in one embodiment the first and second switches 246, 252 are field effect transistors (FETs) 256, 258.

In one embodiment, the control system 240 includes the control buttons 176. A user such as the surgeon or the patient 12 is able to program the control system 240 to deliver medication at the desired flow rate. Based on the desired flow rate, the electronic controller 118 controls energization of the motor 42 to deliver the medication.

In one embodiment, each revolution of the motor 42 delivers a set amount of the medication during a known period of time. In order to meet the desired flow rate, the electronic controller 118 calculates a period of time between revolutions of the motor 42.

In one embodiment, the motor control circuit 242 includes the motor sensor 254 (see FIG. 4). The motor sensor 254 is coupled to the motor 42 and is adapted to detect a revolution of the motor 42 and to responsively generate a motor revolution signal in response to completion of the motor 42 revolution. In one embodiment, the motor sensor 254 is a opto-coupler sensor which is adapted to detect the presence of an indicating flag 260 (see FIG. 5) connected to the motor 42. The indicating flag 260 extends from one of the first and second outside cams 64, 66 to assist in monitoring the amount of the medication that has been delivered to the patient 12. The sensor 254 is optically-coupled with the indicating flag 260 to count revolutions of the indicating flag 260. One suitable sensor 254 is available from Omron of Schaumburg, Ill., as model no. EE-SX1109.

In one embodiment, the electronic controller 118 is adapted to reset the watchdog circuit 248 prior to sending control signals to the motor 42 control circuit to energize the motor 42. The watchdog circuit 248 is adapted to place the second switch 252 in the opened state if two motor revolution signals are received without the watchdog circuit 248 being reset.

In other words, the electronic controller 118 must reset the watchdog circuit 248 prior to or between each revolution of the motor 42. Thus, if a failure of the electronic controller 118 or the microprocessor 244 erroneously causes a control signal to be delivered to the motor control circuit 242 to continuously place the first switch 246 in the closed state, and thus, to erroneously energize the motor 42, the second switch 252 will be placed in the opened state. With the second switch 252 in the opened state, power will not be delivered to the motor 42.

Additionally, if a failure of the first switch 246 leaves the first switch 246 in the closed state, successive motor revolution signals will be received by the watchdog circuit 248 without the watchdog circuit 248 being reset and the watchdog circuit 248 will place the second switch 252 in the opened state, thus preventing power from being supplied to the motor 42.

In one embodiment, the electronic controller 118 is adapted to track the time after a motor control signal has been sent and to enter a disabled state if the time between the sent control signal and received motor revolution signal exceeds a predetermined threshold.

With specific reference to FIG. 26, in one embodiment the monitor circuit 248 includes first and second flip-flops 262, 264. The first flip-flop 262 is coupled to the electronic controller 118 and the second flip-flop 264. The second flip-flop 264 is coupled to the second FET 258.

In the illustrated embodiment, the first and second flip-flops 262, 264 are JK flip-flops. The inverse output ($\overline{Q}$) of the second flip-flop 264 is connected to the gate of the second FET 258. The clock input (CLK) of the second flip-flop 264 is coupled to the output (Q) of the first flip-flop 262. Power is supplied by the microprocessor 244 to the first and second flip-flops 262, 264 to the J and K inputs of the first flop 262 and to the J input of the second flip-flop 264. The drain of the second FET 258 is coupled to the first FET 256 and the source of the second FET 258 is connected to electrical ground.

The watchdog circuit 248 is reset by shutting off and restoring power to the first and second flip-flops 262, 264, to the J and K inputs of the first flop 262, and to the J input of the second flip-flop 264. In one embodiment, the electronic controller 118 shuts off power to the first and second flip-flops 262, 264 after each revolution of the motor 42 and supplies power prior to turning on the first switch 246 to begin the next cycle. This has two effects: conserving power and resetting the first and second flip-flops 262, 264.

The clock input (CLK) of the first flip-flop 262 is connected to the output of the motor sensor 254. The clock input (CLK) of the first flip-flop 262 is also connected to the microprocessor 244 via a third FET 266. The third FET 266 provides isolation between the microprocessor 244 and the motor sensor 254 and the monitor circuit 248. This isolation prevents a shorted pin on the electronic controller 118 from preventing revolution pulses from reaching the flip-flops 262, 264.

The inverse clear input ($\overline{CLR}$) of the first and second flip-flops 262, 264 are coupled to the microprocessor 244 via a buffer circuit 268. In the illustrated embodiment, the buffer circuit 268 includes a first buffer 270, a first resistor 272 and a capacitor 274. The electronic controller 118 may continuous supply power to the motor 42 by turning on the first switch 246 and continuously resetting the first and second flip-flops 262, 264 through the inverse clear inputs without turning off power to the flip-flops 262, 264.

In one embodiment, the flip-flops 262, 264 are triggered by logic level high ("HIGH") to logic level low ("LOW") transitions. The buffer circuit 268 prevents erroneous signal transitions when the input to the buffer circuit 268 is held HIGH by the microprocessor 244.

With specific reference to FIG. 27, the motor control circuit 242 includes the first FET 256 and the opto-coupler sensor 276. A flashback diode 278 is coupled across first and second motor junctions 280A, 280B. The opto-coupler sensor 276 is coupled to the second motor junction 280B. The transmitting diode of the opto coupler sensor 276 is coupled to power (V+) and ground through switch 256. In this arrangement the sensor 276 is only powered during the time the motor 42 is running thus conserving battery life. An output of the opto-coupler sensor 276 is coupled to the third transistor 266 via a second buffer 282.

The gate of the first FET 256 is coupled to the microprocessor 244. The drain of the first FET 256 is coupled to the motor 42 and the source of the first FET 256 is connected to the drain of the second FET 258.

As described above, the electronic controller 118 is adapted to supply medication by energizing the motor 42. A desired flow rate is achieved by energizing the motor 42 and waiting between revolutions of the motor 42 for a calculated period of time. The motor 42 is energized by turning on the first FET 256. In the illustrated embodiment, the first FET 256 is turned on by the microprocessor 244 by changing the state of the gate of the first FET 256 from LOW to HIGH. If the second FET 258 is also on, then power flows through the motor 42 and the first and second FETs 256, 258. When the motor 42 has made one (1) complete revolution, then the output of the motor sensor 254 transitions from HIGH to LOW. In the illustrated embodiment, this transition is the motor revolution signal. The motor revolution signal is also transmitted to the microprocessor 244 via the third FET 266. After receiving the motor revolution signal the microprocessor 244 turns off the first FET 256 by changing the state of the gate of the first FET 256 from HIGH to LOW.

During normal operation, the microprocessor 244 then turns off power to the first and second flip-flops 262, 264. As described above, based on the desired flow rate and the known quantity of medication delivered per revolution of the motor 42, the microprocessor 244 calculates a wait period between motor revolutions. After the wait period (or right before the wait period ends), the microprocessor 244 restores power to the first and second flip-flops 262, 264. As discussed above, this resets the first and second flip-flops 262, 264. Then the microprocessor 244 may again turn on the first FET 256 to energize the motor 42.

If a failure condition of the control system 240 exists, such as a microprocessor 244 failure or other failure, and the watchdog circuit 248 is not reset, then watchdog circuit 248 turns off the second FET 258, thereby preventing power from being supplied to the motor 42.

For example, if the microprocessor 244 fails while the first FET 256 is on, then the motor 42 will continue to be energized. The motor sensor 254 will generate motor revolution signals each time a motor revolution is completed. However, the microprocessor 244 does not or is unable to reset the watchdog circuit 248. Two successive motor revolution signals received on the CLK input of the first flip-flop 262 without the watchdog circuit 248 being reset will flip the inverse output of the second flip-flop 264 (from HIGH to LOW) and thus turn off the second FET 258.

Likewise, a failure of the first transistor 256 in the closed state will continuously energize the motor 42. If the microprocessor 244 does not reset the watchdog circuit 248, then successive motor revolution signals received on the CLK input of the first flip-flop 262 will flip the inverse output of the second flip-flop 264 and thus turn off the second FET 258.

With the second FET 258 in the off state, power will not be delivered to the motor 42.

Returning to FIG. 25, the control system 240 further includes a key 284 which is connected to the electronic controller 118 only during initialization. In one embodiment, the key 284 is part of the testing instrument 200 which is also used to test the control system 240 after it has been assembled and the batteries 45 are installed. Upon initial power-up, the control system 240 will only initialize if the key 284 is present. If the key 284 is not present, then the control system 240 enters a disabled mode and medication cannot be delivered.

In one embodiment, upon initial power-up the control system 240 sends a signal to the key 284. If present, the key 284 delivers a return signal to the control system 240 indicating its presence. The use of the key 284 ensures that the system 10 cannot be improperly reset by removing and then re-inserting the batteries 45 or other power supply 43. If this occurs and the key 284 is not present, the system 10 will not work.

The control system 240 includes a crystal 285 coupled to the microprocessor 244. The crystal 285 controls the frequency at which the microprocessor 244 operates in a conventional manner. However, if the crystal 285 is operating improperly, the microprocessor 244 could begin to operate at either a higher frequency or a lower frequency than intended. The microprocessor 244 also includes an internal oscillator 286. In one embodiment, the control system 240 is adapted to compare a frequency of the crystal 285 with a frequency associated with the internal oscillator 286. The electronic controller 118 adapted to compare a difference between the first and second frequencies and enter a disabled state if the difference is greater than a predetermined threshold. Thus, if the crystal 285 experiences a failure, the control system 10 will be disabled.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that reference numerals are merely for convenience and are not to be in any way limiting, the invention may be practiced otherwise than as specifically described.

What is claimed is:

1. A pump assembly for an integrated medication delivery system, wherein said pump assembly delivers medication to a patient and is suitable to prevent inadvertent delivery of the medication to the patient, said assembly comprising:
   a pump housing having a pump inlet and a pump outlet;
   a first pinch lever disposed at said pump inlet, said first pinch lever being moveable between an open position and a closed position to control a flow of the medication into said pump housing through said pump inlet;
   a second pinch lever disposed at said pump outlet, said second pinch lever being moveable between an open position and a closed position to control a flow of the medication from said pump housing through said pump outlet;
   a motor operatively engaging said first and second pinch levers for moving said first and second pinch levers into said open position such that the medication can be delivered to the patient; and
   at least one compression spring engaging at least one of said first and second pinch levers to urge at least one of said first and second pinch levers toward the flow of medication, while working in conjunction with said motor to normally bias at leasr one of said first and second pinch levers into said closed position during delivery of the medication to the patient and to maintain at least one of said first and second pinch levers in said closed position during a failure of said motor to prevent the inadvertent delivery of the medication to the patient.

2. A pump assembly as set forth in claim 1 further comprising a cam shaft supported on said pump housing and geared to said motor to operatively engage said motor with said first and second pinch levers.

3. A pump assembly as set forth in claim 2 wherein each of said first and second pinch levers comprise a cam follower, said cam followers being engaged by said cam shaft for alternating movement of said first and second pinch levers between said open and closed positions such that the medication can be delivered to the patient.

4. A pump assembly as set forth in claim 2 further comprising a piston disposed in said pump housing, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position.

5. A pump assembly as set forth in claim 4 wherein said piston comprises an actuation end and a pumping end with a diaphragm seal disposed at said pumping end.

6. A pump assembly as set forth in claim 5 wherein said actuation end of said piston comprises at least one slot, and said pump housing comprises at least one detent engaging said at least one slot to prevent unwanted rotation of said piston as said piston is moved within said pump housing by said motor.

7. A pump assembly as set forth in claim 5 wherein said cam shaft supports first and second outside cams and an inside cam disposed between said first and second outside cams, said first outside cam engaging said first pinch lever to move said first pinch lever between said open and closed position, said inside cam engaging said actuation end of said piston to move said piston within said pump housing, and said second outside cam engaging said second pinch lever to move said second pinch lever between said open and closed positions.

8. A pump assembly as set forth in claim 7 wherein each of said first and second pinch levers comprise a cam follower, said cam follower of said first pinch lever being engaged by said first outside cam for alternating movement of said first pinch lever between said open and closed positions, and said cam follower of said second pinch lever being engaged by said second outside cam for alternating movement of said second pinch lever between said open and closed positions.

9. A pump assembly as set forth in claim 8 wherein each of said first and second outside cams comprise internal cam surfaces, said cam follower of said first pinch lever riding within said internal cam surface of said first outside cam for alternating movement of said first pinch lever between said open and closed positions, and said cam follower of said second pinch lever riding within said internal cam surface of said second outside cam for alternating movement of said second pinch lever between said open and closed positions.

10. A pump assembly as set forth in claim 7 further comprising an indicating flag extending from one of said first and second outside cams for monitoring an amount of the medication that has been delivered to the patient.

11. A pump assembly as set forth in claim 10 in combination with a sensor optically-coupled with said indicating flag to count revolutions of said indicating flag for monitoring the amount of the medication that has been delivered to the patient.

12. A pump assembly as set forth in claim 7 wherein each of said first and second outside cams comprise a plurality of slits along an outer circumference of said cams to confirm dimensional tuning of said cams during assembly.

13. A pump assembly as set forth in claim 7 wherein at least one of said first and second outside cams comprises an assembly slot defined within an outer circumference of said cams to facilitate assembly of said pump assembly.

14. A pump assembly as set forth in claim 1 wherein said motor moves said first and second pinch levers into said open position despite said bias of said at least one compression spring such that the medication can be delivered to the patient.

15. A pump assembly as set forth in claim 1 wherein said at least one compression spring comprises a first and a second compression spring, said first compression spring engaging said first pinch lever and said second compression spring engaging said second pinch lever to maintain said first and second pinch levers in said closed position during a failure of said motor to prevent the inadvertent delivery of the medication to the patient.

16. A pump assembly for an integrated medication delivery system, wherein said pump assembly delivers medication to a patient and is suitable to prevent inadvertent delivery of the medication to the patient, said assembly comprising:
a pump housing having inlet and a pump outlet;
a first pinch lever disposed near said pump inlet, said first pinch level being moveable between an open position and a closed position to control a flow of the medication into said pump housing through said pump inlet;
a second pinch level disposed near said pump outlet, said second pinch lever being moveable between an open position and a closed position to control a flow of the medication from said pump housing through said pump outlet;
a motor operatively engaging said first and second pinch levers for moving said first and second pinch levers into said open position such that the medication can be delivered to the patient;
at least one biasing device engaging at least one of said first and second pinch levers and working in conjunction with said motor to normally bias at least one of said first and second pinch levers into said closed position during delivery of the medication to the patient and to maintain at least one of said first and second pinch levers in said closed position during a failure of said motor to prevent the inadvertent delivery of the medication to the patient;
a piston disposed in said pump housing and including an actuation end and a pumping end, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position; and
a diaphragm seal disposed at said pumping end of said piston.

17. A pump assembly for an integrated medication delivery system used to deliver medication to a patient, said assembly comprising:
a pump housing having a pump inlet and a pump outlet;
a first pinch lever disposed near said pump inlet, said first pinch lever being moveable between an open position and a closed position and to control a flow of the medication into said pump housing through said pump inlet;
a second pinch lever disposed near said pump outlet, said second pinch lever being moveable between an open position and a closed position to control a flow of the medication from said pump housing through said pump outlet;
a motor operatively engaging said first and second pinch levers for moving said first and second pinch levers into said open position such that the medication can be delivered to the patient;
a piston disposed in said pump housing and including an actuation end having at least one slot formed therein, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position; and
at least one detent on said pump housing engaging said at least one slot to prevent unwanted rotation of said piston is moved within said pump housing by said motor.

18. A pump assembly for an integrated medication delivery system used to deliver medication to a patient, said assembly comprising:
a pump housing having a pump inlet and a pump outlet;
a first pinch lever disposed near said pump inlet, said first pinch lever being moveable between an open position and a closed position to control a flow of the medication into said pump housing through said pump inlet;

a second pinch lever disposed near said pump outlet, said second pinch lever being moveable between an open position and a closed position to control a flow of the medication from said pump housing through said pump outlet;

a motor operatively engaging said first and second pinch levers for moving said first and second pinch levers into said open position such that the medication can be delivered to the patient;

a piston disposed in said pump housing and including an actuation end and a pumping end, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position;

a cam shaft supported on said pump housing and geared to said motor to operatively engage said motor with said first and second pinch levers wherein said cam shaft supports first and second outside cams and an inside cam disposed between said first and second outside cams, said first outside cam engaging said first pinch lever to move said first pinch lever between said open and closed positions, said inside cam engaging said actuation end of said piston to move said piston within said pump housing, and said second outside cam engaging said second pinch lever to move said second pinch lever between said open and closed positions; and an indicating flag extending from one of said first and second outside cams for monitoring an amount of the medication that has been delivered to the patient.

19. A pump assembly as set forth in claim 18 in combination with a sensor optically-coupled with said indicating flag to count revolutions of said indicating flag for monitoring the amount of the medication that has been delivered to the patient.

20. A pump assembly for an integrated medication delivery system, wherein said pump assembly delivers medication to a patient and is suitable to prevent inadvertent delivery of the medication to the patient, said assembly comprising:

a pump housing having a pump inlet and a pump outlet;

a first pinch lever disposed near said pump inlet, said first pinch lever being moveable between an open position and a closed position to control a flow of the medication into said pump housing through said pump inlet;

a second pinch lever disposed near said pump outlet, said second pinch lever being moveable between an open position and a closed position to control a flow of the medication from said pump housing through said pump outlet;

a motor operatively engaging said first and second pinch levers for moving said first and second pinch levers into said open position such that the medication can be delivered to the patient;

at least one biasing device engaging at least one of said first and second pinch levers and working in conjunction with said motor to normally bias at least one of said first and second pinch levers into said closed postion during delivery of the medication to the patient and to maintain at least one of said first and second pinch levers in said closed position during a failure of said motor to prevent the inadvertent delivery of the medication to the patient;

a piston disposed in said pump housing and including an actuation end and a pumping end, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position;

a medication inlet tube adapted to provide access for the medication to flow into said pump inlet;

a medication outlet tube adapted to provide access for the medication to flow from said pump outlet; and wherein said at least one biasing device engages said first pinch lever to normally-bias said first pinch lever into said closed position to pinch said medication inlet tube, and said at least one biasing device engages said second pinch lever to normally-bias said second pinch lever into said closed position to pinch said medication outlet tube.

21. A pump assembly for an integrated medication delivery system, wherein said pump assembly delivers medication to a patient and is suitable to prevent inadvertent delivery of the medication to the patient, said assembly comprising:

a pump housing having a pump inlet and a pump outlet;

a first pinch lever disposed near said pump inlet, said first pinch lever being moveable between an open position and a closed position to control a flow of the medication into said pump housing through said pump inlet;

a second pinch lever disposed near said pump outlet, said second pinch lever being moveable between an open position and a closed position to control a flow of the medication from said pump housing through said pump outlet;

a motor operatively engaging said first and second pinch levers for moving said first and second pinch levers into said open position such that the medication can be delivered to the patient;

at least one biasing device engaging at least one of said first and second pinch levers and working in conjunction with said motor to normally bias at least one of said first and second pinch levers into said closed position during delivery of the medication to the patient and to maintain at least one of said first and second pinch levers in said closed position during a failure of said motor to prevent the inadvertent delivery of the medication to the patient;

a piston disposed in said pump housing and including an actuation end and a pumping end, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position; and an actuator engaging said first and second pinch levers to retain both said first and second pinch levers in said open position for sterilization despite said bias of said at least one biasing device.

22. A pump assembly for an integrated medication delivery system, wherein said pump assembly delivers medication to a patient and is suitable to prevent inadvertent delivery of the medication to the patient, said assembly comprising;

a pump housing having a pump inlet and a pump outlet;

a first pinch lever disposed near said pump inlet, said first pinch lever being moveable between an open position and a closed position to control a flow of the medication into said pump housing through said pump inlet;

a second pinch lever disposed near said pump outlet, said second pinch lever being moveable between an open position and a closed position to control a flow of the medication from said pump housing through said pump outlet;

a motor operatively engaging said first and second pinch levers for moving said first and second pinch levers into said open position such that the medication can be delivered to the patient;

a piston disposed in said pump housing and including an actuation end and a pumping end, said motor moving said piston within said pump housing to draw the medication into said pump housing when said first pinch lever is in said open position and said second pinch lever is in said closed position, and to displace the medication from said pump housing when said first pinch lever is in said closed position and said second pinch lever is in said open position;

a cam shaft supported on said pump housing and geared to said motor to operatively engage said motor with said first and second pinch levers wherein said cam shaft supports first and second outside cams and an inside cam disposed between said first and second outside cams, said first outside cam engaging said first pinch lever to move said first pinch lever between said open and closed position, said inside cam engaging said actuation end of said piston to move said piston within said pump housing, and said second outside cam engaging said second pinch lever to move said second pinch lever between said open and closed positions; and wherein each of said first and second outside cams comprise a plurality of slits along an outer circumference of said cams to confirm dimensional tuning of said cams during assembly.

23. A pump assembly for an integrated medication delivery system, wherein said pump assembly delivers medication to a patient and is suitable to prevent inadvertent delivery of the medication to the patient, said assembly comprising:

a pump housing having a pump inlet and a pump outlet;

a first pinch lever disposed near said pump inlet, said first pinch lever being moveable between an open position and a closed position to control a flow of the medication into said pump housing through said pump inlet;

a second pinch lever disposed near said pump outlet, said second pinch lever being moveable between an open position and a closed position to control a flow of the medication from said pump housing through said pump outlet;

a motor operatively engaging said first and second pinch levers for moving said first and second pinch levers into said open position such that the medication can be delivered to the patient;

at least one biasing device engaging at least one of said first and second pinch levers to urge at least one of said first and second pinch levers toward the flow of medication, while working in conjunction with said motor to normally bias at least one of said first and second pinch levers into said closed position during delivery of the medication to the patient and to maintain at least one of said first and second pinch levers in said closed position during a failure of said motor to prevent the inadvertent delivery of the medication to the patient; and a cam shaft supported on said pump housing and geared to said motor to operatively engage said motor with said first and second pinch levers wherein each of said first and second pinch levers comprise a cam follower, said cam followers being engaged by said cam shaft for alternating movement of said first and second pinch levers between said open and closed positions such that the medication can be delivered to the patient.

* * * * *

UNITED STATES PATENT AND TRADEMARK OFFICE
CERTIFICATE OF CORRECTION

PATENT NO. : 7,048,715 B2  Page 1 of 1
APPLICATION NO. : 10/234400
DATED : May 23, 2006
INVENTOR(S) : Diaz et al.

It is certified that error appears in the above-identified patent and that said Letters Patent is hereby corrected as shown below:

In Column 28, line 13, Claim 1, delete the first occurrence of "at" and please replace with - - near - -.

In Column 28, line 17, Claim 1, delete the first occurrence of "at" and please replace with - - near - -.

In Column 28, line 30, Claim 1, delete the first occurrence of "leasr" and please replace with - - least - -.

In Column 29, line 61, Claim 16, after the first occurrence of "having" please insert - - a pump - -.

In Column 29, line 63, Claim 16, delete the first occurrence of "level" and please replace with - - lever - -.

In Column 29, line 66, Claim 16, delete the first occurrence of "level" and please replace with - - lever - -.

Signed and Sealed this

Twenty-second Day of August, 2006

JON W. DUDAS
*Director of the United States Patent and Trademark Office*